(12) United States Patent
Reydel

(10) Patent No.: US 9,833,126 B2
(45) Date of Patent: Dec. 5, 2017

(54) BALLOON ACCESS DEVICE WITH FEATURES FOR ENGAGING AN ENDOSCOPE

(71) Applicant: Visualization Balloons, LLC, West Caldwell, NJ (US)

(72) Inventor: Boris Reydel, West Caldwell, NJ (US)

(73) Assignee: Visualization Balloons, LLC, West Caldwell, NJ (US)

(*) Notice: Subject to any disclaimer, the term of this patent is extended or adjusted under 35 U.S.C. 154(b) by 262 days.

(21) Appl. No.: 14/568,993

(22) Filed: Dec. 12, 2014

(65) Prior Publication Data

US 2015/0119640 A1 Apr. 30, 2015

Related U.S. Application Data

(63) Continuation-in-part of application No. 13/439,977, filed on Apr. 5, 2012, now Pat. No. 9,220,396.
(Continued)

(51) Int. Cl.
*A61B 1/00* (2006.01)
*A61B 1/04* (2006.01)
(Continued)

(52) U.S. Cl.
CPC ...... *A61B 1/00082* (2013.01); *A61B 1/00089* (2013.01); *A61B 1/00096* (2013.01); *A61B 1/00101* (2013.01); *A61B 1/00137* (2013.01); *A61B 1/018* (2013.01); *A61B 1/31* (2013.01); *A61B 17/00234* (2013.01);
(Continued)

(58) Field of Classification Search
CPC ............ A61B 1/00082; A61B 1/00101; A61B 1/00089; A61B 1/00137; A61B 1/273; A61B 1/2733; A61B 1/2736; A61B 1/31; A61B 1/00096; A61B 2017/0034;
(Continued)

(56) References Cited

U.S. PATENT DOCUMENTS 3,417,745 A 12/1968 Emanuel
3,690,769 A 9/1972 Mori
(Continued)

FOREIGN PATENT DOCUMENTS

CN 101453936 6/2006
EP 0112148 6/1984
(Continued)

OTHER PUBLICATIONS

International Search Report and Written Opinion for corresponding International Application No. PCT/US14/70049, dated Mar. 18, 2015, 9 pages.
(Continued)

*Primary Examiner* — Ryan Henderson
(74) *Attorney, Agent, or Firm* — Meunier Carlin & Curfman LLC

(57) ABSTRACT

A balloon access device for use with an endoscope is disclosed. A transparent balloon attached to the distal end of the endoscope allows a user to both separate collapsed intestinal tissue and visualize the path of the endoscope without administering insufflation gas to the collapsed area of a patient. The attachment of the balloon to the endoscope is achieved by the various embodiments of the balloon access device disclosed herein.

29 Claims, 19 Drawing Sheets

Related U.S. Application Data

(60) Provisional application No. 61/471,957, filed on Apr. 5, 2011, provisional application No. 61/963,734, filed on Dec. 13, 2013, provisional application No. 61/997,865, filed on Jun. 12, 2014.

(51) Int. Cl.
*A61B 1/06* (2006.01)
*A61M 29/00* (2006.01)
*A61B 1/018* (2006.01)
*A61B 1/31* (2006.01)
*A61B 17/00* (2006.01)
*A61M 25/10* (2013.01)

(52) U.S. Cl.
CPC .. *A61B 2017/0034* (2013.01); *A61M 25/1002* (2013.01); *A61M 25/1009* (2013.01)

(58) Field of Classification Search
CPC ............ A61M 25/104; A61M 25/1034; A61M 25/1006; A61M 25/10
USPC ........ 600/101, 104, 106, 107, 115–116, 127, 600/129, 153, 154, 175–177; 604/96.01–103.08, 103.13, 103.14, 104
See application file for complete search history.

(56) References Cited

U.S. PATENT DOCUMENTS

| | | | |
|---|---|---|---|
| 3,866,599 A | 2/1975 | Johnson | |
| 4,619,247 A | 10/1986 | Inoue et al. | |
| 4,681,093 A | 7/1987 | Ono et al. | |
| 4,841,952 A | 6/1989 | Sato et al. | |
| 4,961,738 A | 10/1990 | Mackin | |
| 5,002,556 A | 3/1991 | Ishida et al. | |
| 5,029,574 A | 7/1991 | Shimamura et al. | |
| 5,030,227 A | 7/1991 | Rosenbluth et al. | |
| 5,103,804 A | 4/1992 | Abele et al. | |
| 5,257,617 A | 11/1993 | Takahashi | |
| 5,271,383 A | 12/1993 | Wilk | |
| 5,304,173 A | 4/1994 | Kittrel et al. | |
| 5,337,730 A | 8/1994 | Maguire | |
| 5,364,353 A | 11/1994 | Corfitsen et al. | |
| 5,681,344 A | 10/1997 | Kelly | |
| 5,855,569 A | 1/1999 | Komi | |
| 5,897,487 A | 4/1999 | Ouchi | |
| 6,056,719 A | 5/2000 | Mickley | |
| 6,059,719 A | 5/2000 | Yamamoto et al. | |
| 6,142,945 A * | 11/2000 | Sakamoto .............. | A61B 1/018 600/459 |
| 6,306,081 B1 | 10/2001 | Ishikawa et al. | |
| 6,423,055 B1 | 7/2002 | Farr et al. | |
| 6,953,431 B2 | 10/2005 | Barthel | |
| 8,574,289 B2 | 11/2013 | Cartledge et al. | |
| 2002/0068853 A1 | 6/2002 | Adler | |
| 2003/0233142 A1 | 12/2003 | Morales et al. | |
| 2005/0049461 A1 | 3/2005 | Honda et al. | |
| 2005/0288552 A1 | 12/2005 | Barthel | |
| 2006/0025654 A1 | 2/2006 | Suzuki et al. | |
| 2006/0106414 A1 | 5/2006 | Fogarty et al. | |
| 2007/0015966 A1 | 1/2007 | Niwa et al. | |
| 2007/0249907 A1 | 10/2007 | Boulais et al. | |
| 2007/0276180 A1 | 11/2007 | Greenburg et al. | |
| 2007/0287885 A1 | 12/2007 | Brown | |
| 2009/0082626 A1 | 3/2009 | Ichimura et al. | |
| 2009/0287050 A1 | 11/2009 | Barthel | |
| 2010/0274084 A1 | 10/2010 | Barthel | |
| 2012/0232342 A1 | 9/2012 | Reydel | |
| 2012/0259175 A1 | 10/2012 | Reydel et al. | |

FOREIGN PATENT DOCUMENTS

| | | |
|---|---|---|
| JP | 63/201504 | 8/1988 |
| JP | 01/221133 | 9/1989 |
| JP | 2005/503203 | 2/2005 |
| JP | 2007/175502 | 7/2007 |
| JP | 2008/212506 | 9/2008 |
| JP | 2009/534113 | 9/2009 |
| WO | 2011/047339 | 4/2011 |
| WO | 2012/138815 | 10/2012 |

OTHER PUBLICATIONS

Office Action from European Application No. 10824218.1 dated Mar. 1, 2013.
English Translation of Office Action for Japanese Application No. 2012-534419 dated Feb. 18, 2014.
International Search Report and Written Opinion for corresponding International Application No. PCT/US2012/032248, dated Jul. 2, 2012, 14 pages.
International Search Report and Written Opinion for corresponding International Application No. PCT/US2010/052947, dated May 27, 2011, 6 pages.
Preliminary Report on Patentability from corresponding International Application No. PCT/US2010/052947, dated Apr. 17, 2012, 6 pages.
Supplementary European Search Report and European Search Opinion, issued by the European Patent Office in Application No. EP 14870480.2 dated Aug. 8, 2017, 7 pages.

* cited by examiner

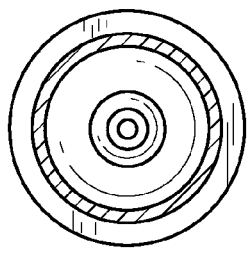 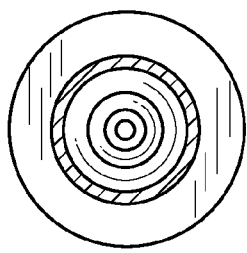 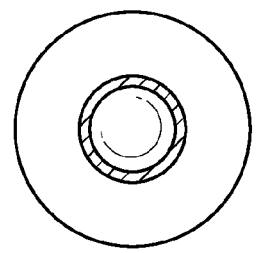
*FIG. 26B*  *FIG. 26C*  *FIG. 26D*

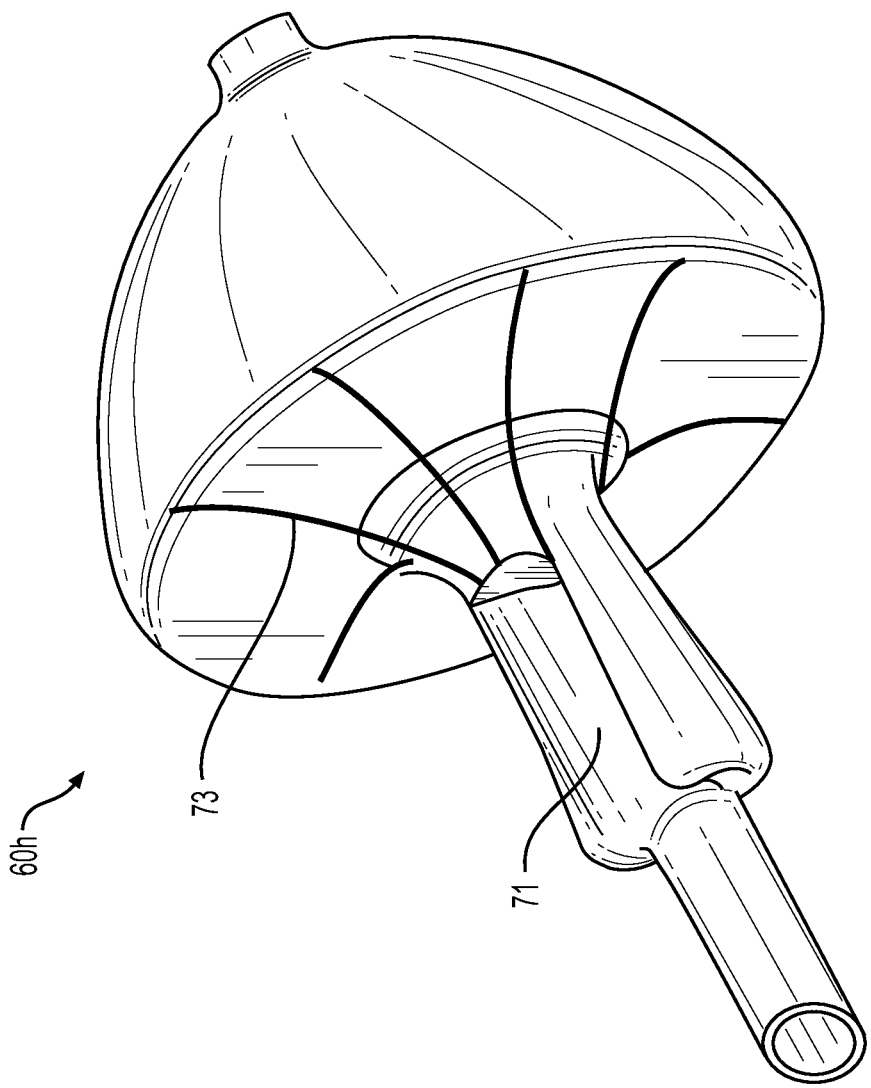

BALLOON ACCESS DEVICE WITH FEATURES FOR ENGAGING AN ENDOSCOPE

RELATED APPLICATIONS

This is a continuation-in-part of U.S. patent application Ser. No. 13/439,977, filed Apr. 5, 2012, which claims the benefit of U.S. Provisional Application No. 61/471,957, filed Apr. 5, 2011. This application also claims the benefit of U.S. Provisional Applications 61/963,734, filed Dec. 13, 2013, and 61/997,865, filed Jun. 12, 2014. Each of these applications are incorporated by reference in their entireties for all purposes.

TECHNICAL FIELD

The present apparatus embodied relates, in general, to medical devices and in particular, to access balloons for use with endoscopes.

BACKGROUND

Endoscopes are well-known in the art and are flexible devices that are inserted into a natural body orifice such as the mouth or anus to provide visual and surgical access to portions of the upper and lower gastrointestinal (GI) tract. Endoscope accessible portions of the lower GI tract extend from the anus to the small intestine, and during this journey, the flexible endoscope must traverse a torturous convoluted path through the anus, the rectum, and through the large intestine to the ileocecal opening of the small intestine. The torturous path includes an "S" shaped passage through the rectosigmoid junction and the sigmoid colon, and around several larger than right angled bends of the splenic flexure and hepatic flexure. Additionally, in small bowel enteroscopy, an endoscope must traverse a large torturous convoluted path having multiple "S" shaped passages.

Before insertion of the endoscope, the patient is given drugs to purge fecal matter from the lower GI tract. Once emptied, the tubular walls of the large intestine can flatten or collapse together into a flattened tubular configuration. The collapsed intestines may inhibit passage of the flat face of the distal end of the endoscope, and the collapsed tissue can inhibit visualization by pressing against or near to a camera mounted within the flat face. To enhance the passage of the endoscope through the collapsed lower GI tract and to improve visualization, insufflation gas is routinely pumped into the patient's lower GI tract to expand and distend the collapsed tubular tissues. The expanded walls may improve visualization and reduce tissue contact with the flat face of the endoscope as it is pushed farther and farther into the insufflated lower GI tract. The distal portion of the endoscope is steerable, and the insufflated tissue can provide room for the surgeon to visually steer the endoscope through the path ahead.

The administration of insufflation gas to the lower GI tract can induce abdominal discomfort, and this has led to the common practice of anesthetizing the patient during the procedure. Additionally, insufflation gas may cause lengthening of anatomy and spontaneous perforation. Post-surgical recovery times are provided to allow the patient to purge insufflation gas and to awaken from the anesthesia. $CO_2$ is commonly used for insufflation as it is more readily absorbed through the patient's intestinal wall to reduce the post-operative recovery time. $CO_2$ gas control systems, $CO_2$ tanks, and $CO_2$ gas heaters must be purchased and maintained in order to provide $CO_2$ as an insufflation gas.

SUMMARY

The present invention provides a balloon access device for use with an endoscope. The balloon access device allows a physician to both separate collapsed tissue and visualize the path of the endoscope without administering insufflation gas to the collapsed area of a patient.

In one embodiment, the balloon access device includes a balloon expandable from a deflated shape to an inflated shape, the balloon having a proximal end and a distal end, wherein a dome portion is formed on the distal end of the balloon, and a cap having a proximal end configured to be coupled to a distal end of an endoscope and a distal end for sealing with the proximal end of the balloon when the balloon is expanded.

In another embodiment, the inflated shape includes a non-pressurized shape and a fully inflated shape.

In still another embodiment, the proximal end of the balloon includes a proximal collar configured to couple to a distal end of a catheter and a sealing surface configured to seal with the cap.

In yet another embodiment, the cap includes an endoscope receptacle extending into the cap through the proximal end of the cap for receiving the distal end of the endoscope.

In a further embodiment, the cap includes a stop that engages a front face of the endoscope when the endoscope is received within the cap, and wherein an opening is provided through the stop to distally expose at least one of a light, opening, optics or operative channel on the front face of the endoscope.

In another embodiment, the cap includes a balloon sealing portion proximate the distal end of the cap, the balloon sealing portion including a circular groove that retains and seals with a circular rib of the balloon.

In still another embodiment, the cap includes an outwardly flaring balloon sealing portion that is flexible outwardly relative to a body of the cap to create a seal with the balloon.

In yet another embodiment, the outwardly flaring balloon sealing portion prevents the balloon from being unseated from the cap.

In a further embodiment, the cap includes a rib on an interior portion of the cap, and wherein the sealing surface of the balloon nests and seals with a receptacle of a balloon sealing portion and the rib.

In another embodiment, the dome portion is hemispherical or ellipsoidal in shape.

In still another embodiment, the balloon is non-concentrically disposed relative to the endoscope.

In yet another embodiment, the balloon includes a distally located guide tip on a distal portion of the dome portion for guiding an operator in parting and spreading non-insufflated gastrointestinal tissue during operation.

In a further embodiment, the balloon is a transparent hollow balloon.

In another embodiment, the balloon access device includes a lock mechanism for securing a catheter relative to the endoscope to maintain a sealing contact between the balloon and the cap.

In still another embodiment, the lock mechanism includes a releasably lockable clamp mechanism that contacts and grips the catheter.

In yet another embodiment, the balloon access device includes a lock mechanism including a balloon insertion tube for receiving the balloon when the balloon is in the deflated state, the tube having a length greater than a y-portion of an operative channel within the endoscope to guide the balloon into and beyond the y-portion, and a clamp for securing a catheter relative to the endoscope to maintain a sealing contact between the balloon and the cap.

In a further embodiment, the balloon access device includes a balloon insertion tube for receiving the balloon when the balloon is in the deflated state, the balloon insertion tube having a length greater than a y-portion of an operative channel within the endoscope to guide the balloon into and beyond the y-portion.

In another embodiment, the balloon access device is in combination with a catheter, wherein the proximal end of the balloon is coupled to a distal end of the catheter.

In still another embodiment, the balloon access device is in combination with an endoscope, wherein the proximal end of the cap is coupled to the distal end of the endoscope.

In yet another embodiment, the cap is integral with the endoscope.

According to another aspect of the invention, a balloon access device for use with an endoscope is provided. The device includes a balloon expandable from a deflated shape to an inflated shape, the balloon having a proximal end and a distal end, wherein a dome portion is formed on the distal end of the balloon, a cap having a proximal end configured to be coupled to a distal end of an endoscope and a distal end for sealing with the proximal end of the balloon when the balloon is passed through the cap and expanded to the inflated shape, and a balloon insertion tube for receiving the balloon when the balloon is in the deflated state, the balloon insertion tube having a length greater than a y-portion of an operative channel within the endoscope to guide the balloon into and beyond the y-portion.

According to still another aspect of the invention, a method of creating a seal between a balloon and a cap is provided, the balloon having a proximal collar having a base portion and an elongated projecting portion coupled to a distal end of a catheter, and the cap having a proximal end coupled to a distal end of an endoscope, the method including advancing the catheter and balloon through an operative channel of the endoscope until the balloon is positioned distal the distal end of the cap, expanding the balloon from a deflated shape to at least a partially inflated shape, and moving the balloon proximally towards the cap so that the base portion abuts a distal end of the cap to create a seal between the cap and the balloon.

According to yet another aspect of the invention, a method of performing a gastrointestinal procedure on a patient having gastrointestinal tissue in a non-insufflated state using an endoscope and balloon access device installed upon the endoscope is provided, the balloon access device including a cap coupled to a distal end of the endoscope and an at least partially inflated balloon coupled to a distal end of a catheter received in an operative channel of the endoscope, the method including advance the endoscope through the gastrointestinal tissue, guiding the endoscope using a lens on a distal end of the endoscope and a guide tip on a distal end of the balloon, and spreading the tissue using a distal dome portion of the balloon and the guide tip, wherein the balloon is transparent so that an operator can view the tissue through the balloon using the lens and the operator can center the guide tip in a gastrointestinal tract.

In one embodiment, the method includes retracting the endoscope from the gastrointestinal tissue, wherein during the retracting a balloon sealing portion of the cap flattens a luminal fold in the tissue.

Other embodiments of the balloon access device are configured for use with or without a cap. These embodiments are configured for use with an endoscope having an operative channel with a distal opening and a visualization channel.

Balloons for use in these embodiments are inflatable or deflatable, and have a proximal end and a distal end having a dome portion. The proximal end may include a collar having a proximal elongated projecting portion and a base portion located distal to the projecting portion. The projecting portion may be configured to project proximally within the operative channel. The proximal elongated projecting portion has a central long axis. The size of at least two cross sections of the projecting portion differ when taken perpendicular to the central long axis. At least a portion of the proximal end of the balloon is configured for positioning over the visualization channel when the projecting portion projects within the operative channel, such that imaging using the endoscope visualization channel includes the transmission of light through the proximal and distal ends of the balloon.

In some embodiments, the collar includes a shaped portion that is at least one of pyramidal, tapered, frustoconical, or bulbous. The shaped portion may be part of the proximal elongated projecting portion of the collar. In some embodiments, the shaped portion is adjacent to the base portion of the collar. In other embodiments, the shaped portion is spaced from the base portion of the collar. The shaped portion may be tapered. The narrower or the wider end of the taper may be positioned adjacent the base portion of the collar.

In some embodiments, the outer surface of the collar of the balloon may include one or more grooves. The groove(s) may be located on the projecting portion, the base portion, or both. The grooves may extend from a proximal point on the collar to a distal point on the collar. In some embodiments, the grooves may include at least one transverse cross section along their length, the shapes of the transverse cross sections including at least one of a polygon, a sector of a circle or ellipse, and/or a segment of a circle or ellipse. The transverse cross sections may also include multiple portions, and each portion may have the shape of a polygon, a sector of a circle or ellipse, or a segment of a circle or ellipse.

In some embodiments, the collar may include trusses. The trusses may include at least one transverse cross section along their length, the shape of the transverse cross section being at least one of cylindrical, ellipsoidal and/or polygonal. The trusses may extend from at least one proximal point on the collar to at least one distal point on the collar. They may extend along the proximal elongated projecting portion of the collar, and they may continue distally to extend along the base portion of the collar.

In some embodiments, at least one part of the proximal collar comprises a sun beams-shaped pattern in transverse cross section, the sun beams-shaped pattern including multiple rays extending from a central point, and multiple indentations between the rays. At least one indentation of the sun beams pattern is configured to mate with at least one protrusion on an underlying surface. The protrusion(s) may be located on the distal face of the endoscope, the interior lumen of the endoscope, or both. The protrusion may be a lens in optical communication with the visualization channel of the endoscope.

Methods of visualizing the internal surface of an intestinal cavity are also disclosed. The method may include providing a balloon access device, positioning a portion of the system within the intestinal cavity of the patient, moving the catheter within the operative channel of the endoscope such that at least one portion of the balloon is extending beyond a distal end of the endoscope, inflating the balloon, positioning the balloon to promote contact between the base portion of the collar and a lens positioned on the distal face of the endoscope (the lens being in optical communication with the visualization channel of the endoscope), and maneuvering the balloon to visualize of internal surface of the intestinal cavity.

The method may also include assembling the system outside of a patient to promote optimal visualization through the proximal portion of the balloon during operation of the system.

Methods may include activating an optical communication system comprising the lens and the visualization channel of the endoscope.

Methods may include delivering fluid to the intestinal cavity through the operative channel of the endoscope, creating a suction between the intestinal cavity and the operative channel of the endoscope, or both.

Positioning the balloon to promote contact may include pulling the catheter proximally to cause the base portion of the balloon to abut the lens of the endoscope.

In embodiments where at least one part of the collar of the balloon includes a sun beams-shaped pattern in transverse cross section, maneuvering the balloon may include rotating the balloon until at least one indentation mates with at least one protrusion on the endoscope. This protrusion may be a lens on the distal face of the endoscope.

The foregoing and other features of the invention are hereinafter described in greater detail with reference to the accompanying drawings.

DESCRIPTION OF DRAWINGS

FIG. 26B is a tranverse section of a balloon along the section line designated in FIG. 26A.

FIG. 26C is a tranverse section of a balloon along the section line designated in FIG. 26A.

FIG. 26D is a tranverse section of a balloon along the section line designated in FIG. 26A.

FIG. 28 is a perspective view of a balloon including longitudinal grooves and trusses.

DETAILED DESCRIPTION

The following description of certain examples of the medical apparatus should not be used to limit the scope of the medical apparatus. Other examples, features, aspects, embodiments, and advantages of the medical apparatus will become apparent to those skilled in the art from the following description, which is by way of illustration, one of the best modes contemplated for carrying out the medical apparatus. As will be realized, the medical apparatus is capable of other different and obvious aspects, all without departing from the spirit of the medical apparatus. Accordingly, the drawings and descriptions should be regarded as illustrative in nature and not restrictive.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Figure 1:
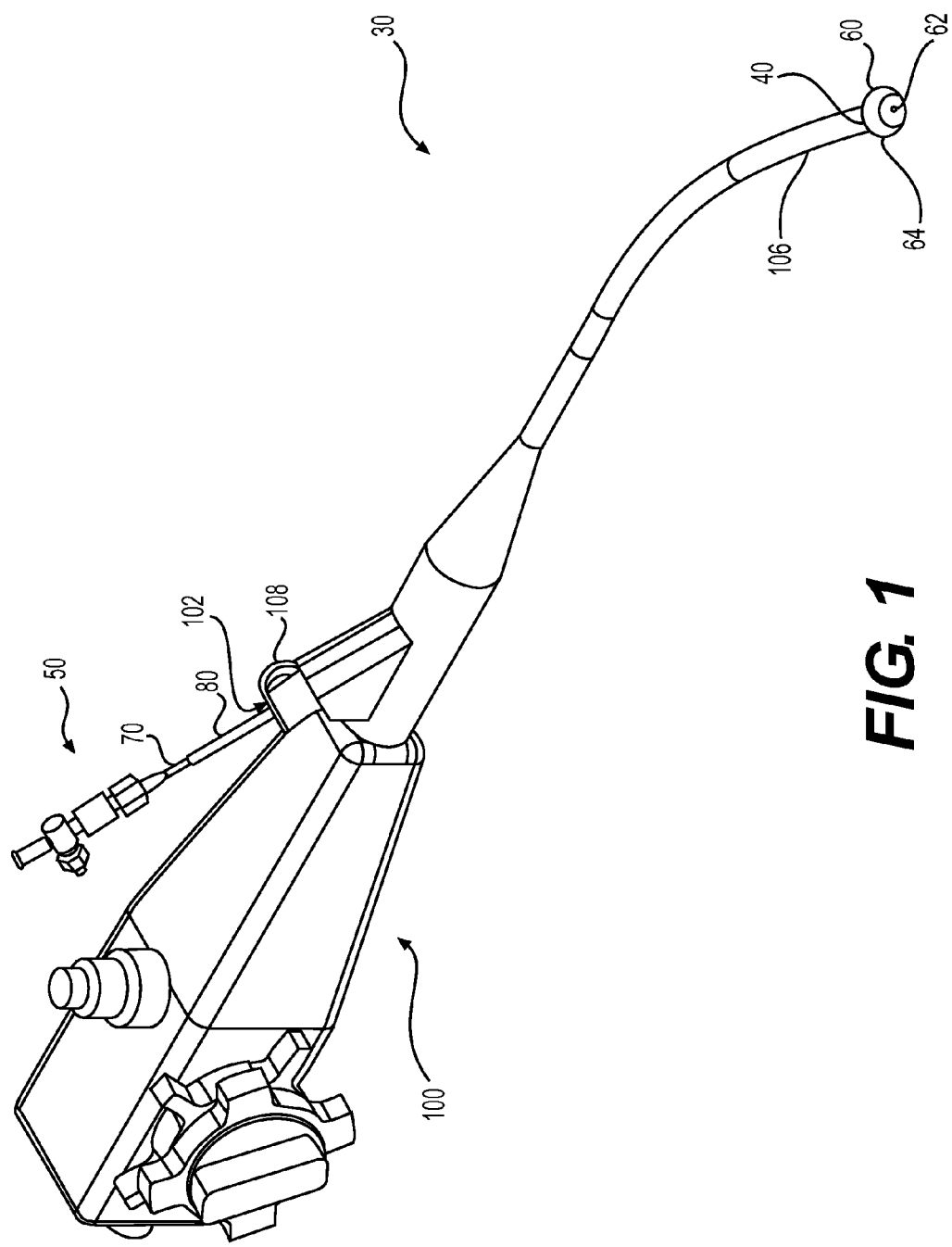
FIG. 1 is an isometric view of an embodiment of a transparent balloon access device deployed on an endoscope.

FIG. 1 is an isometric view of one embodiment of a balloon access device 30 installed upon an endoscope 100. The balloon access device 30 is configured to fit within an operative channel 102 of the endoscope 100 when undeployed, and to deploy a transparent hollow balloon 60 across a distal face 104 of the endoscope 100. The balloon 60 is transparent so that scope optics can view GI tissue there through, and balloon 60 can be dome shaped on at least a distal end. A distally located guide tip 62 is supported solely on a distal end of the dome shape by a membrane wall 65 of the balloon 60. The configuration of the deployed guide tip 62 and balloon 60 on the endoscope 100 is such that non-insufflated GI tissue can be parted and spread with the tip 62 and the balloon 60 in response to pushing with the endoscope 100. The balloon access device 30 and endoscope 100 as configured can rapidly burrow along a non-insufflated and at least partially pinched GI tract such as the non-insufflated lower GI tract, or can pass through an expanded or insufflated portion of the GI tract. As will be described in detail later, the deployed transparent guide tip 62 can be visually aimed at a center of the collapsed lumen of the non-insufflated GI tract by articulating a distal end 106 of the endoscope 100. When the guide tip 62 is aimed, pushing the endoscope 100 initiates the spreading and parting of the collapsed tissue walls with the balloon access device 30, thereby enabling passage of the endoscope 100 along a center of the non-insufflated lumen of the GI tract.

As shown in FIG. 1, the balloon access device 30 is shown inserted into an operative channel 102 of the endoscope 100 and comprises a proximal handle portion 50 extending from a proximal opening of the operative channel 102. A biopsy valve 108 is provided on the proximal opening of the operative channel 102 and a hollow catheter 70 extends from the proximal handle portion 50, through the biopsy valve 108, and into the operative channel 102. A distal end of the catheter 70 is secured to a proximal end of the transparent balloon 60 shown extending across a distally located front face 104 of the endoscope 100.

A balloon seal cap 40 of the balloon access device 30 is removably secured to the distal end 106 of the endoscope 100 and forms a fluid tight seal with at least one surface on a proximal end of the balloon 60. Alternatively, it will be appreciated that the cap 40 may be integral with the endoscope. The seal cap 40 may be any suitable shape, such as cylindrically shaped. The sealing interaction of the seal cap 40 with the endoscope 100, and the balloon 60 with the seal cap 40, can create a sealed volume across the front face 104 of the endoscope 100 to prevent the egress of unwanted fluids across the optical lens 105 of an endoscope camera located on the front face 104 (see FIG. 17). Additionally, once the seal is formed, the balloon 60 can be further secured to the seal cap 40 by applying a vacuum to the operative channel 102 to draw the balloon 60 into further engagement with the seal cap 40. Alternately, a vacuum port (not shown) in the endoscope 100 can be used to draw the balloon 100 against the front face 104 of the endoscope. The balloon device 30 can be rapidly deployed and inflated into place on the endoscope 100 for advancement, and rapidly deflated and withdrawn from the operative channel 102 of the endoscope 100 for the insertion and deployment of another surgical instrument from the operative channel 102 into the lower GI tract. An example of such another surgical instrument can be, but is not limited thereto, a snare or tissue biopsy device to retrieve a tissue sample from a suspect site.

Figure 2:
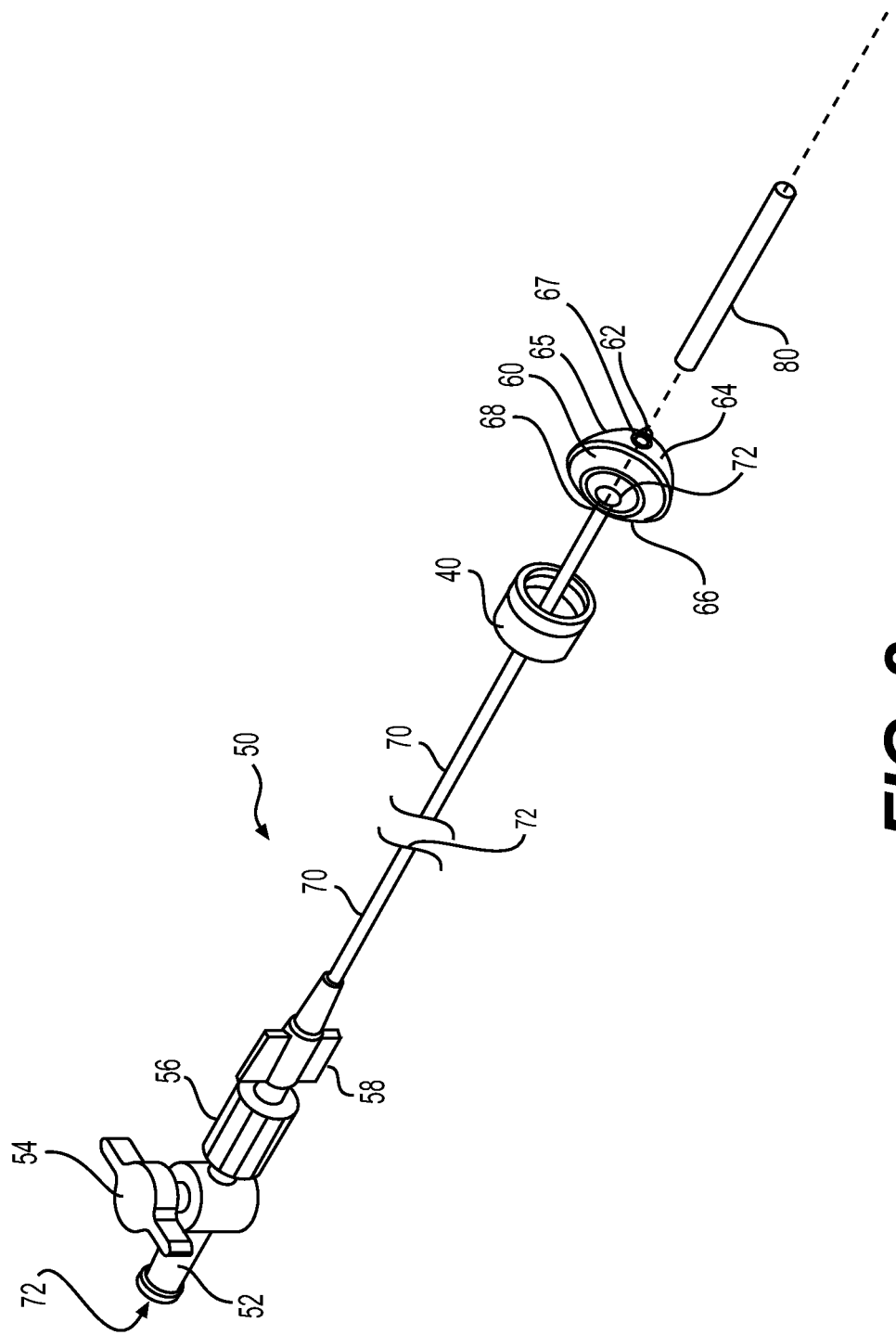
FIG. 2 is an isometric view of the balloon access device with the transparent balloon shown in a normal unexpanded dome shape.

FIG. 2 shows an isometric view of the balloon access device 30. The handle or proximal handle portion 50 includes a hollow passage 72 that extends longitudinally through the handle portion 50, through the hollow catheter 70, and operatively connects to an inner volume of the balloon 60. Handle portion 50 includes a proximal luer lock 52 to removably engage hollow passage 72 with compressed gas and/or vacuum lines and or fluid lines, a valve 54 to control the flow of gas and vacuum to the distal balloon 60, a grip 56, and orientation wings 58. Hollow catheter 70 can be configured to have sufficient length to work with an endoscope 100 as described above, or long enough to work with a variety of endoscopes 100 with differing lengths.

Figure 3:
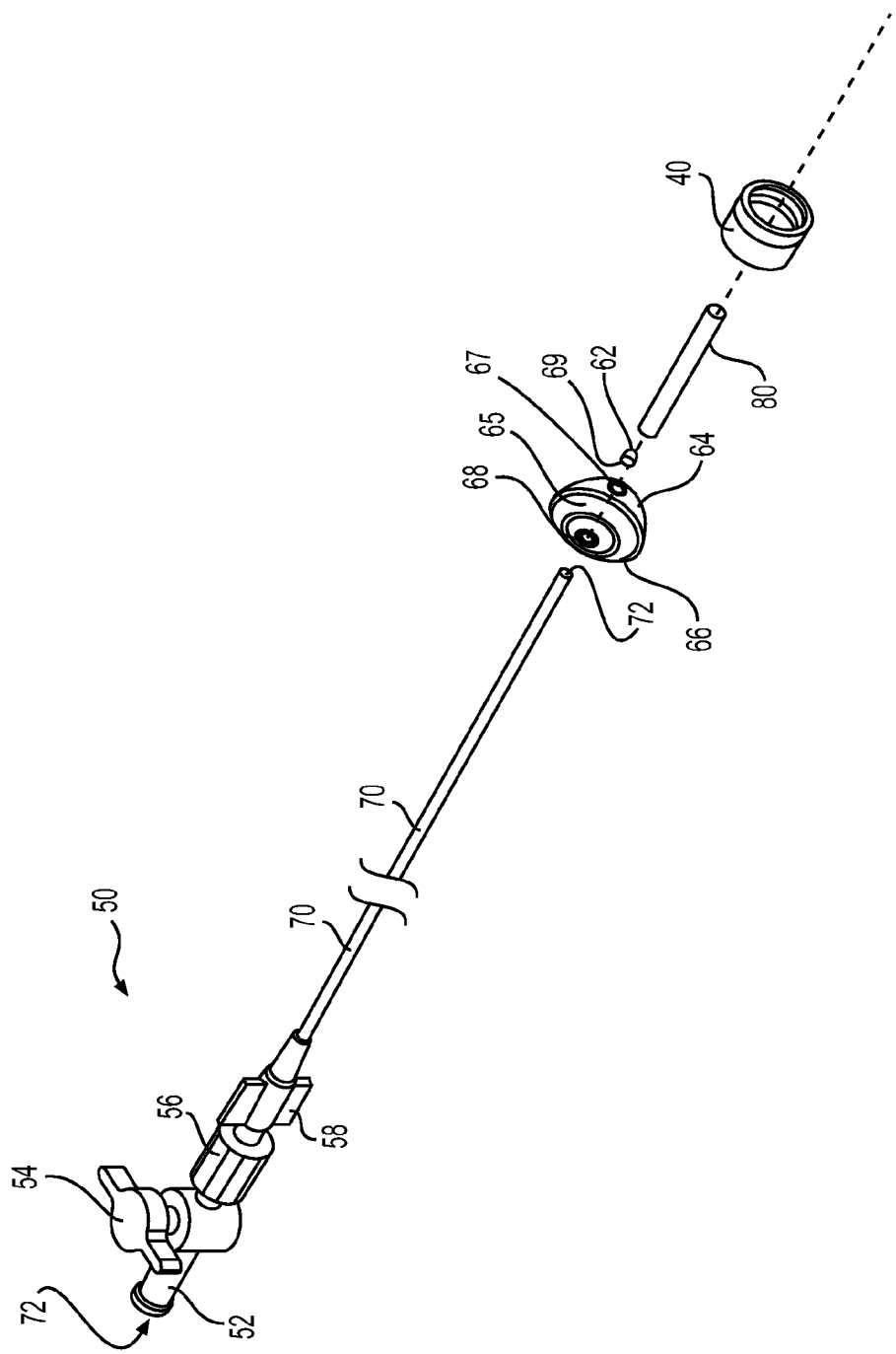
FIG. 3 is an isometric exploded view of the balloon access device.
Figure 4:
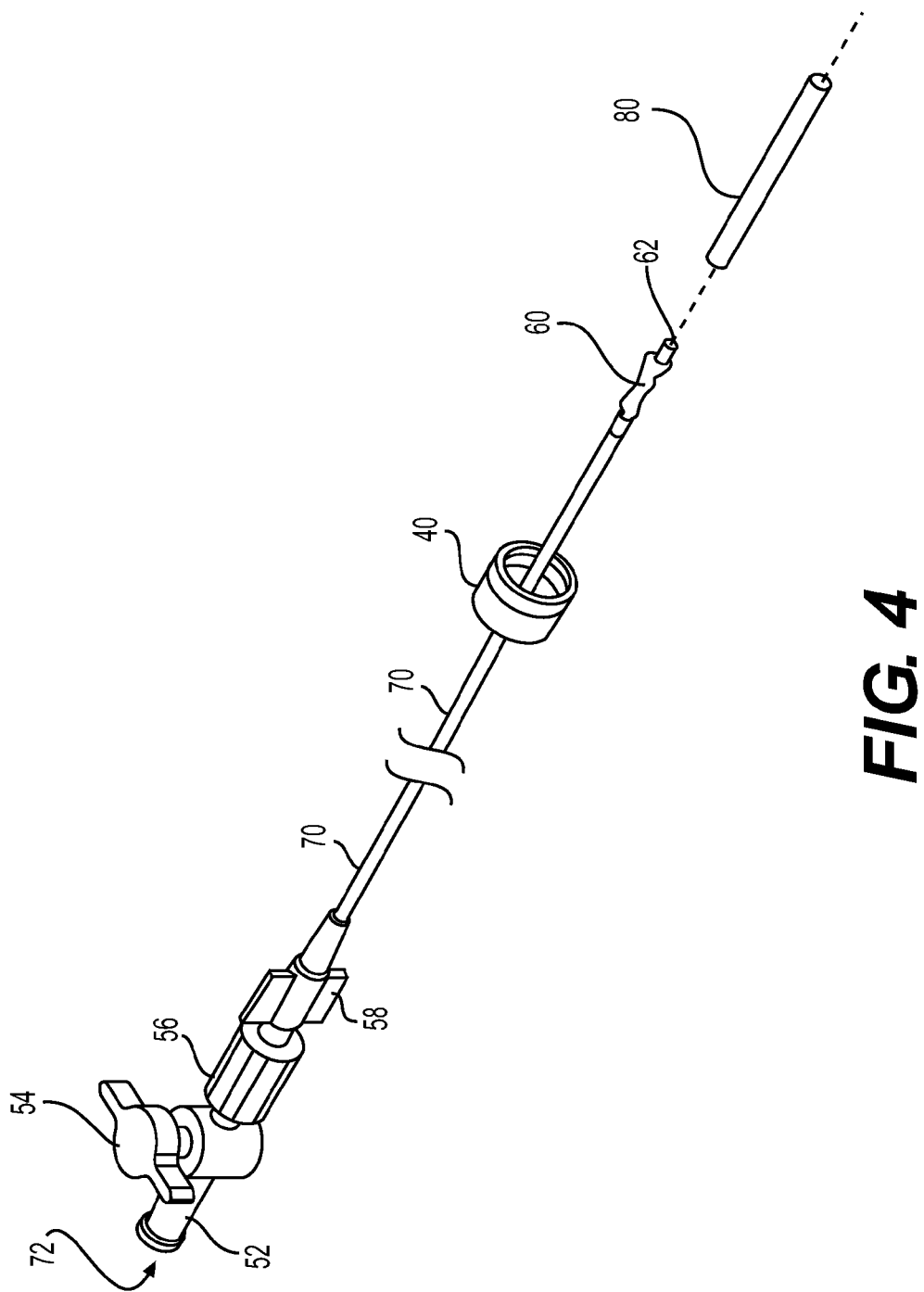
FIG. 4 is an isometric view of the balloon access device with the balloon shown collapsed by drawing a vacuum prior to being inserted into an adjacent balloon insertion tube.

In FIGS. 2 and 3, the transparent balloon 60 is shown in the normal unpressurized or "as manufactured" shape wherein the hollow balloon 60 can have a distal dome 64 and at least one sealing surface 66 on a proximal side. The balloon 60 is configured to be symmetrical and concentric about a longitudinal axis of the balloon 60 and a longitudinal axis of the catheter 70, and the distal dome 64 can be hemispherical or elliptical in shape about the axis. The balloon includes a proximal collar 63 which includes a proximal elongated projecting portion 68 and a base portion 66. The proximal collar 63 securely seals the balloon 60 to the catheter 70 via an attachment method such as but not limited thereto, by an adhesive or a shrink fit as described later. Elongated projecting portion 68 may have a shaped portion that is cylindrical, pyramidal, tapered, or bulbous, and can include a conical or curved portion for engaging with or sealing with the operative channel 102 of endoscope 100. The guide tip 62 can be a separate piece that can be secured to the dome of the balloon 60 in the exemplary manner. As best shown in FIG. 3, the guide tip 62 has a rounded distal tip and a stepped proximal post 69 that can be adhesively secured into a distal collar 67 formed from the balloon membrane 65. Alternately, the guide tip could be a rounded bump formed from the balloon membrane 65, or an injection of sealing material into the distal collar 67 such as a gob of silicone placed inside the distal collar 67. The guide tip 62 can be transparent for visualization therethrough, or can be opaque or translucent. As shown, guide tip 62 is supported by only the balloon membrane 65 which can provide some freedom of motion of the tip 62 relative to the endoscope 100. This freedom of motion can beneficial when navigating through collapsed tissue A hollow balloon insertion tube 80 is shown distal to the guide tip 62 may be provided to receive and store the balloon 60 and tip 62 within when the balloon is deflated by drawing a vacuum prior to being inserted into an adjacent balloon insertion tube 80, and tube 80 can have a length sufficient to guide the balloon 60 and tip 62 into and beyond a "Y" portion of the operative channel 102 within the endoscope 100. A deflated balloon 60 is shown in FIG. 4 just prior to insertion within a hollow of the balloon insertion tube 80. Before insertion, balloon 60 may have one or more deflation folds of the balloon 60 wrapped or twisted about a longitudinal axis of the balloon (not shown) to create a more compact and organized deflated balloon 60.

Figure 5:
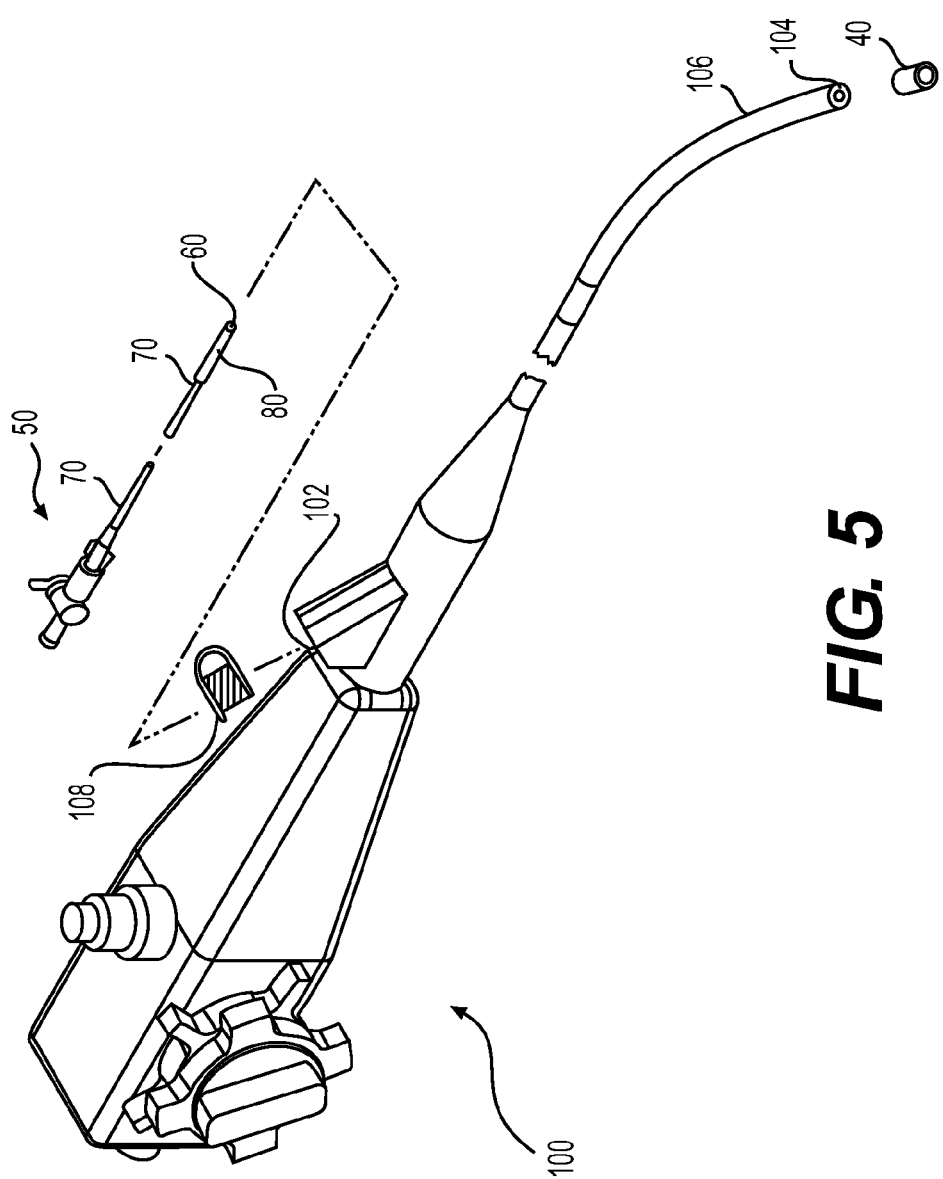
FIG. 5 is an isometric view of the balloon access device with a balloon seal cap placed on a distal end of the scope and with a dashed line illustrating a path where the balloon access device can enter an open instrument channel which exits within the attached balloon seal cap.

FIG. 5 shows the access device 30 ready for installation onto the endoscope 100. In this view, the cylindrical seal cap 40 is positioned for placement onto the distal end 106 of the endoscope 100. The balloon 60 is fully deflated as shown in FIG. 4, and resides within the balloon insertion tube 80. A dashed line is provided to show how the balloon insertion tube 80 of the access device 30 can be inserted into the proximal opening of the operative channel 102 of endoscope 100, and if a biopsy valve 108 is provided, through the biopsy valve 108. The balloon insertion tube 80 can be configured to feed the balloon 60 directly into the operative channel 102 through the balloon insertion tube 108 with the guide tip 62 leading the collapsed balloon. Balloon insertion tube 80 can be the length as shown, or can be longer to guide the collapsed balloon past a "Y" within operative channel 102 Balloon insertion tube 80 can be constructed from a slick or lubricious plastic such as PTFE, or can be lubricated to reduce egress of the collapsed balloon 60 into or out of the tube 80. FIG. 1 shows how the balloon insertion tube 80 can be retracted proximally around the catheter 70 to a position adjacent to the handle portion 50 after the full insertion of the access device 30 into the operative channel 102.

Figure 6:
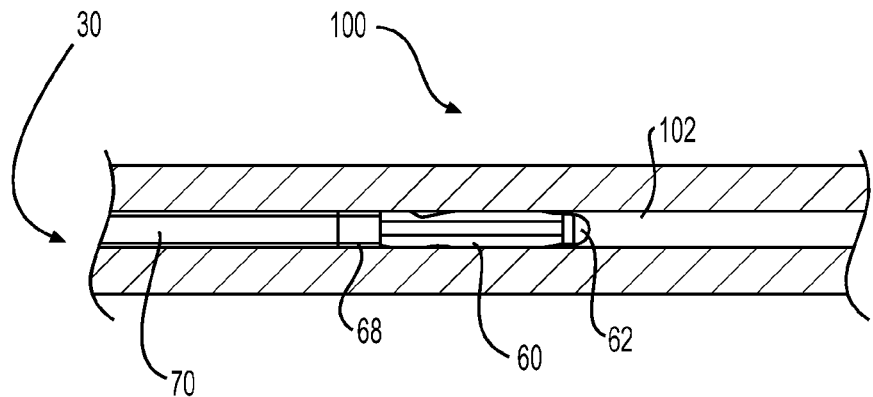
FIG. 6 is a side section view of the flexible shaft of the endoscope with an un-inflated balloon being pushed longitudinally along an instrument passage of the endoscope.

FIG. 6 shows the fully deflated balloon as it is being pushed down channel 102 of the endoscope 100 prior to emergence of the balloon 60 from the distal face 40 of the endoscope 100. The guide tip 62 can be configured with a tip diameter that is close to the inner diameter of the operative channel 102 of the endoscope 100, and an appropriate length so that the tip 62 will not cock and jam within the operative channel 102 of the scope 100. The tip of the guide tip 62 can be any shape that is conducive to steering the guide tip along the operative channel 102 such as the rounded tip 62 shown, or any other guiding shape such as but not limited to a cone.

Figure 7:
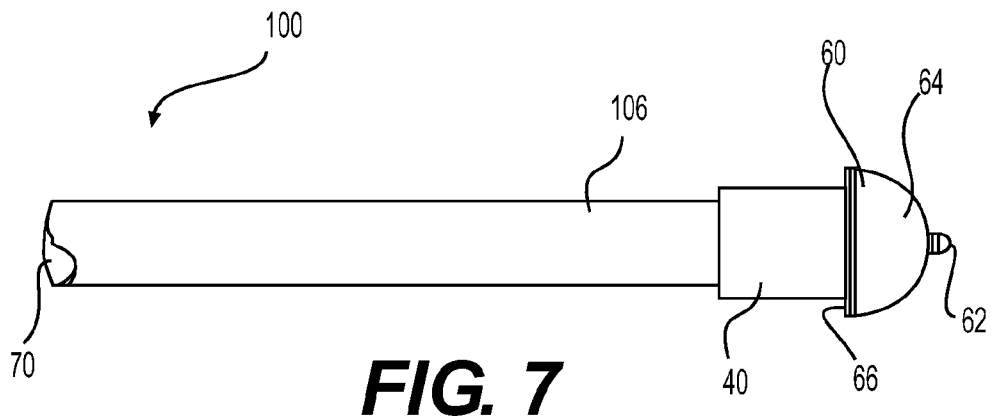
FIG. 7 is a side view showing the balloon after emerging from a distal end of the endoscope.

FIG. 7 shows the balloon 60 after emerging from the distal end 106 of the endoscope 100. Once the balloon 60 is extended from the endoscope 60 and beyond the seal cap 40, atmospheric air may be induced through the hollow passage 72 to allow the balloon 60 to expand into the non-pressurized shape as shown. Once the balloon 60 is fully inflated with a fluid, such as air, to an operating pressure or volume, the balloon 60 is pulled proximally in the direction of the arrow to engage the balloon 60 with the seal tip 40. This pulling of the balloon 60 to seal against the seal tip 40 can be accomplished by pulling on the catheter 70 or the handle portion 50 outside of the patient. If required, the balloon 60 is free to pivot somewhat about the attachment point to the catheter 70 to center itself in the seal cap 40.

Figure 8:
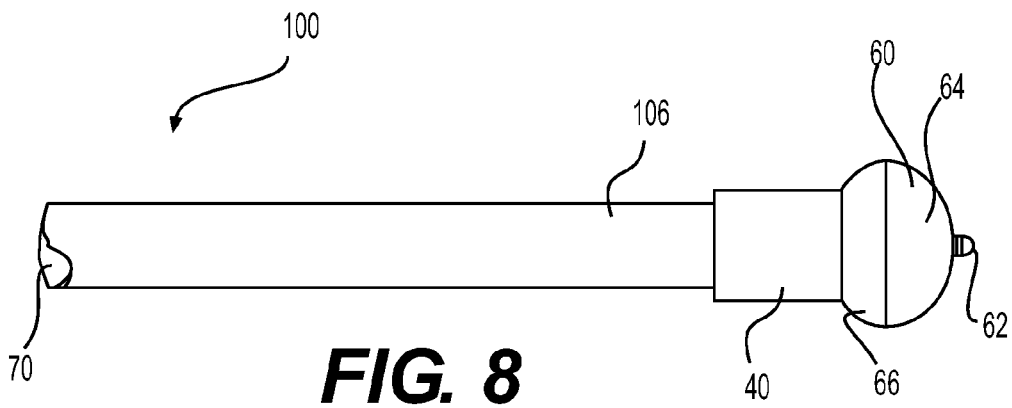
FIG. 8 is a side view showing the balloon inflated after emerging from a distal end of the endoscope.

FIG. 8 shows the fully inflated balloon 60 pulled against the seal cap 40 at the distal end 106 of the endoscope 100. In this view, it can be seen that the inflation of the balloon 60 has changed the at least one base portion 66 of proximal collar 63 into a rounded dome that has maintained a fluid-tight seal with the seal cap 40. The rounding of the at least one base portion 66 has moved the distal dome 64 distally, and the distal dome 64 has expanded both in diameter and longitudinally as shown. The inflation of the balloon 60 can be accomplished prior to insertion of the endoscope 100 into the patient, or after insertion of the endoscope 100 into the natural orifice such as the anus of the patient.

FIGS. 9 through 12 shows exploded cross sectional views of alternate exemplary embodiments of the balloon 60, and balloon seal cap 40 of the present apparatus. The guide tip 62 is also depicted. The exemplary and previously described embodiment of balloon 60 and seal cap 40 is best shown in FIGS. 2, and 3, and is shown in cross section in FIG. 11. The reader is advised to note that the balloon access device 30 is not limited to the previously described embodiment of FIG. 11, nor to the alternate embodiments of FIGS. 9-10 and 12, nor to any of the materials or manufacturing techniques described. Since many of the embodiments of the balloons and seal caps have features that perform the same function, like numbers are identified with sub-identifiers and are meant to correspond to like features on alternate embodiments. For example, a balloon 60 in one embodiment may become a balloon 60a in another alternate embodiment. If differences in functions exist between like numbers such as base portions 66 and 66a, the description associated with the number and sub-identifier will prevail for that embodiment. All embodiments described below have a balloon 60, 60a. 60b, 60c and a seal cap 40, 40a, 40b, 40c.

Figure 11:
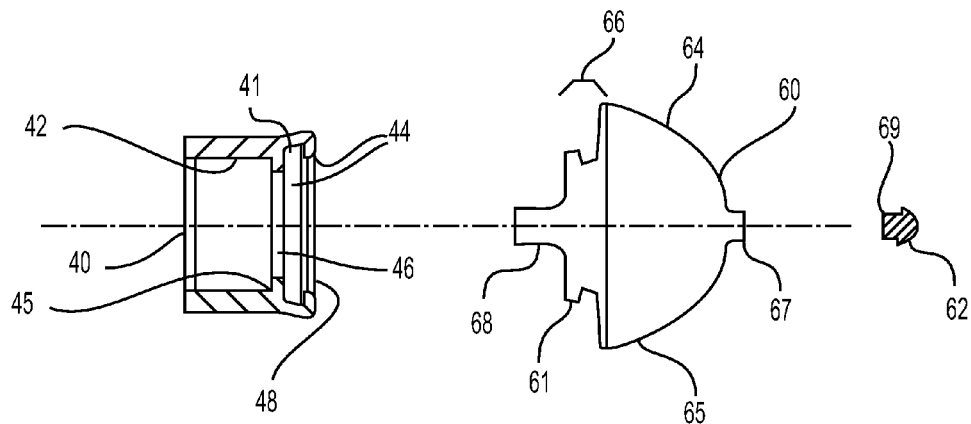
FIG. 11 shows an exploded cross sectional view of an embodiment of the balloon and balloon seal cap.

The embodiment of FIG. 11 comprises the hollow balloon 60, the balloon seal cap 40 and the guide tip 62. This embodiment uses a ring-in-groove seal between the balloon and seal cap 40. The balloon 60 comprises the previously described distal dome 64, the membrane 65, and the at least one base portion 66 of the proximal collar 63. With this embodiment of the balloon 60, the at least one base portion 66 of the balloon comprises two distinct portions. The first portion comprises a circular rib 61 that rings the longitudinal axis of the balloon 60 and is configured to engage with and seal with the circular groove 41 in the seal cap 40. The second portion of the at least one base portion 66 is a dish shaped portion that extends substantially radially inwardly between the largest diameter of distal dome 64 to the circular rib portion. The dish shaped portion can be configured to seal against at least a distalmost surface 48 of the cap 40. The distal collar 67 of balloon 60 extends distally from the dome 64 and is configured to seal with the distal tip 62. The elongated projecting portion 68 of the proximal collar extends proximally from the at least one base portion 66 and is configured to seal with the hollow catheter 70 (see FIGS. 2 and 3).

The balloon seal cap 40 of FIG. 11 comprises a hollow cylinder having an endoscope receptacle 42 extending into a proximal end of the seal cap 40 to receive and seal with the distal end 106 of the endoscope 100. A circular rib 45 can be provided at a distal end of the endoscope receptacle 42 to act as a stop that engages the front face 104 of the endoscope 100 once the scope 100 is fully received within the seal cap 40. An opening 46 is provided through the rib 45 to distally expose the optics, lights, and openings on the endoscope front face 104. A balloon sealing portion 44 extends distally from the rib 45 and includes the previously described circular groove 41 to retain and seal with the circular rib 61 of the balloon 60. The distalmost surface 48 of the balloon sealing portion 44 can seal with the balloon 60. As shown, the receptacle 42, the opening 46, and the balloon sealing portion 44 comprise the open hollow of the cylindrical seal cap 40.

Figure 9:
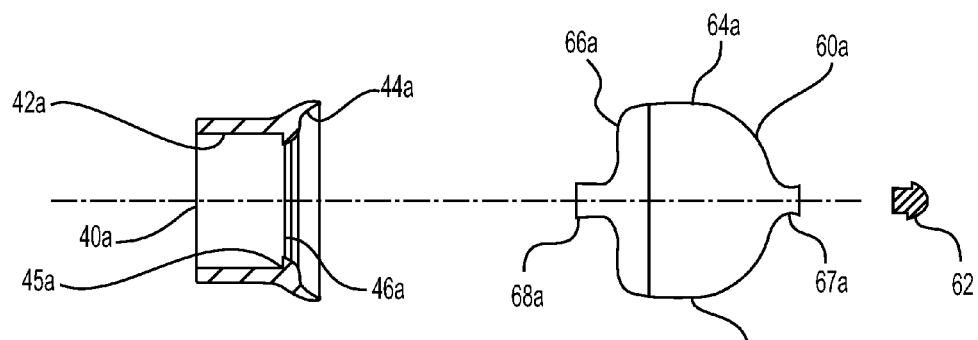
FIG. 9 shows an exploded cross sectional view of an embodiment of the balloon and balloon seal cap.

The embodiment of FIG. 9 comprises a balloon 60a and a seal cap 40a and is configured to provide a ball-in-socket type of sealing. The balloon 60a has a substantially curved base portion 66a that nests within and seals with an outwardly flaring cuplike balloon sealing portion 44a of the seal cap 40a. Seal cap 40a can be configured to flare outward to provide a larger support for the balloon 60a and can exceed the diameter of the endoscope 100. Seal cap 40a is a hollow cylinder that further comprises an endoscope sealing receptacle 42a, circular rib 45a, opening 46a, as well as the previously described balloon sealing portion 44a. Balloon 60a includes a distal dome 64a, a membrane 65a, a distal collar 67a, and a proximal elongated projecting portion 68a. Cuplike balloon sealing portion 4 a of the seal cap 40a can also be used to flatten luminal folds, for example to discern pathologies behind the luminal folds.

Figure 10:
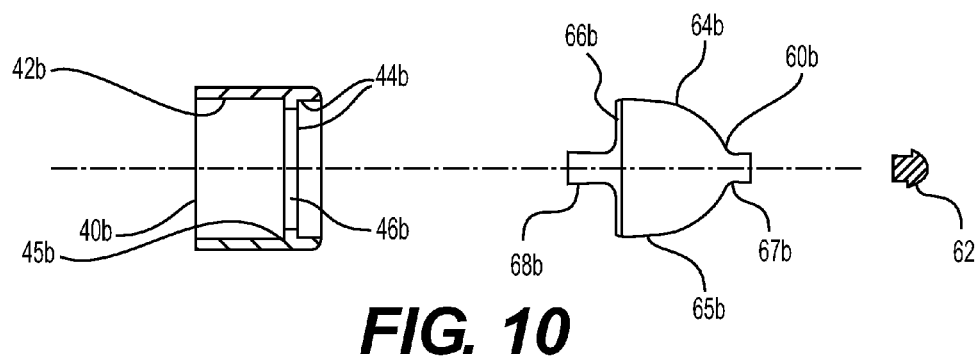
FIG. 10 shows an exploded cross sectional view of an embodiment of the balloon and balloon seal cap.

The embodiment of FIG. 10 comprises a balloon 60b and a seal cap 40b and uses a peg-in-hole arrangement for sealing. In this embodiment, the balloon 60b is sized to have about the same radial diameter as the distal end 106 of the endoscope and the balloon 60b nests and seals with a receptacle of a cylindrical balloon sealing portion 44 a. Mushroom shaped balloon 60a comprises a distal dome 64 with at least one base portion 66a that is substantially flat and circular. Balloon 6 b is configured to fit snugly in the cylindrical balloon sealing portion 44a and to seal the at least one sealing surface 66a against a rib 45b. Cylindrically shaped cap 40b further comprises an endoscope sealing receptacle 42b, and an opening 46b extending through rib 45b. Balloon 60b includes a distal dome 64b, a membrane 65b, a distal collar 67b, and an elongated projecting portion 68b.

Figure 12:
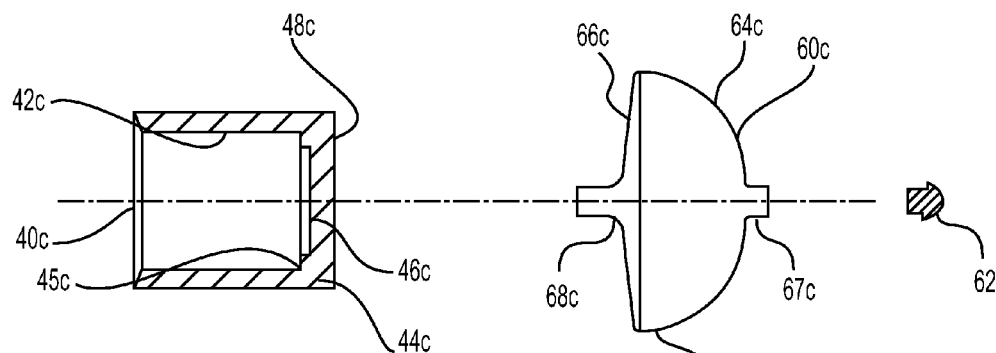
FIG. 12 shows an exploded cross sectional view of an embodiment of the balloon and balloon seal cap.

The embodiment of FIG. 12 comprises a balloon 60c and seal cap 40c that is configured to provide a flat-to-flat seal as the balloon 60c is pulled against a distalmost surface 48c of seal cap 40c. As the inflating balloon 60c changes shape from the mushroom shape to a rounded elliptical ball shape, the seal can move to a beveled portion of a distal balloon sealing portion 44c. Balloon 60c may be substantially mushroom shaped with a substantially flat at least one sealing surface 66c adjacent to a dome 64c. Unlike the embodiment of FIG. 10, the balloon 60c is larger than an outer diameter of a seal cap 40c and overhangs the seal cap 40c. Cylindrically shaped cap 40c further comprises an endoscope sealing receptacle 42c, circular rib 45c, and opening 46c. Balloon 60a further comprises a distal dome 64a, a membrane 65a, a distal collar 67a, and an elongated proximal projecting portion 68a.

The balloons 60, 60a, 60b, and 60c are transparent and can be constructed from a substantially rigid balloon material or an elastomeric material.

Substantially rigid materials cannot expand greatly beyond the normal "as made" shape when inflated and many such materials are well known in the art for use as expansion balloons for cardiac stent deployment products. Elastomeric balloons are expandable, and can comprise material such as, for example, some grades or durometers of elastomers such as polyurethane, latex, natural rubbers, silicones and the like.

The seal caps 40, 40a, 40b, and 40c can comprise a substantially rigid material such as a thermoform plastic, a thermoset plastic, or a metal. With rigid embodiments of the caps, it is the deformation of the balloon 60, 60a, 60b, and 60c against the rigid cap that creates the seal. In yet another embodiment, the seal caps 40, 40a, 40b, and 40c can comprise an elastomeric material such as but not limited to a polyurethane, a polyethylene, silicone, rubber and the like. As such, the elastomeric properties of this embodiment can have sufficient rigidity to generally support the balloon against normal surgical operating forces, yet provide atraumatic characteristics, should substantial resistance be encountered. Rigidity of the elastomeric material could be altered by changing a durometer of the material during manufacturing.

Alternately, the distal balloon sealing portion 44, 44a, 44b, 44c of the caps 40, 40a, 40b, and 40c could be rigid or elastomeric and can further comprise one or more deformable gasket materials to create a seal such as but not limited to: an elastomeric lip seal, an o-ring, an over-molded elastomer, or a foam seal (not shown). Such seals can seal with the balloon 40, the endoscope 100 or both.

The distal guide tip 62 can be used with any balloon embodiments such as 60, 60a, 60b, and 60c. The distal guide tip 62 can include the stepped proximal post 69 which is configured to fit within the distal collar 67, 67a, 67b, or 67c to create a smooth exterior when mated with the balloon 60, 60a, 60b, or 60c (see at least FIGS. 1 & 2). The guide tip 62 and catheter 70 can be adhered to the balloon 60, 60a, 60b, or 60c with adhesives such as but not limited to polyurethanes or cyanoacrylates. Or, alternate fastening techniques can be used with distal guide tip 62 and catheter 70 such as but not limited to heat staking, ultrasonically welding, or laser welding. Whereas these fastening techniques are described for the attachment of the distal guide tip 62, they can be used for all other embodiments of the apparatus such as elements of the handle portion 50 or attachment of the proximal collar 63 to the catheter 80.

FIGS. 13-16 are side views that detail the inflation of the distal portion of the balloon access device 30 on the endoscope 30. The mushroom shaped balloon 60c and cap 40c are the embodiments shown in cross section in FIG. 12. For this inflation description, only the embodiment of FIG. 12 will be described, and the description is based on physical measurements of an actual balloon 60c and cap 40c as the balloon 60c is inflated.

Figure 13:
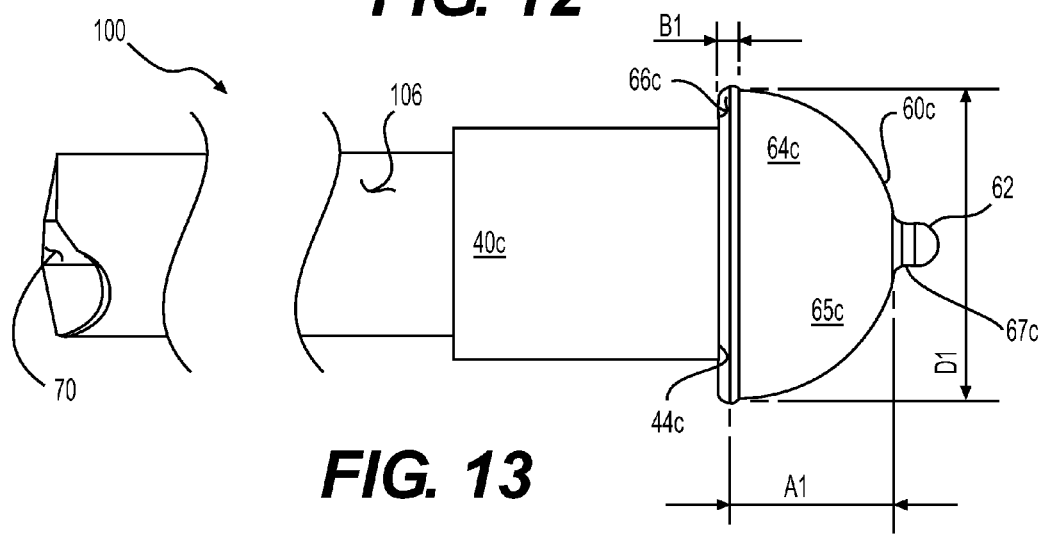
FIG. 13 shows the balloon of FIG. 12 in a normal un-inflated shape wherein the inner air pressure is the same as the outside atmospheric pressure.

FIG. 13 shows balloon 60c in a normal un-inflated normal shape wherein the inner air pressure is the same as the outside atmospheric pressure and the balloon 60c has assumed the "as manufactured" mushroom shape. As shown, the normal shape of balloon 60c is substantially mushroom shaped, and comprises the distal dome 64c attached to the proximal at least one base portion 66c. The at least one base portion 66c is substantially flat and has been pulled back (via catheter 70) to seal against a ring of contact with the ring shaped distalmost surface 48c of the seal cap 40. With atmospheric pressure within balloon 60c, and the valve 54 of the handle portion 50 closed, the balloon 62 is very flaccid and the guide tip 62 is substantially supported by only the membrane 65c. Pushing the guide tip 62 towards the catheter 70 creates a large indention crater with the tip 62 standing proud within as the tip 62 is completely pushed into the dome 64c. Measurements of the balloon 60c of FIG. 13 show an outer dimension D1 of about 18 mm at the widest diameter, and the sum of longitudinal lengths A1 and B1 equal about 11 mm. The balloon 60c and catheter 70 of the actual test balloon 60c required about 2-2.1 ml of air to arrive at the flaccid shape of FIG. 13.

Figure 14:
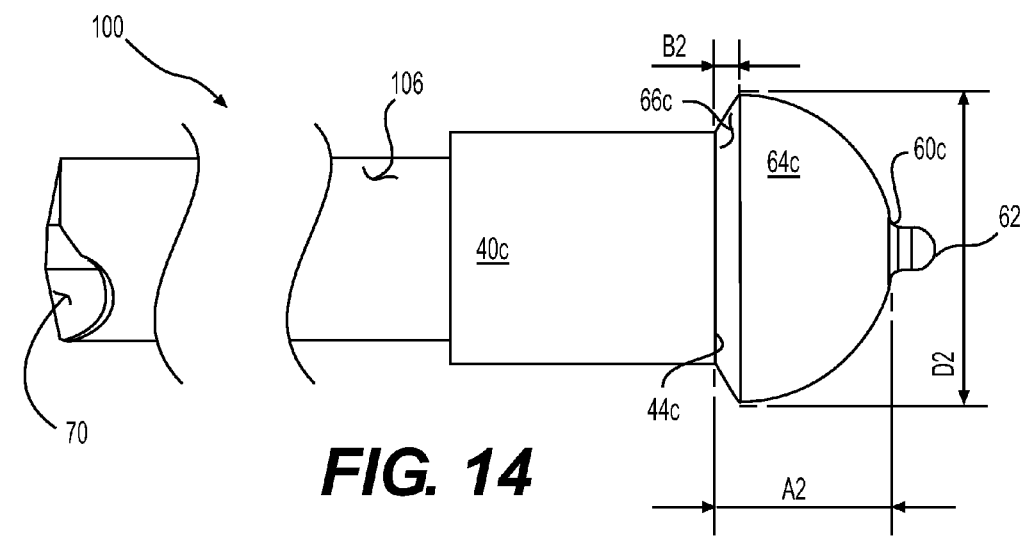
FIG. 14 shows the balloon of FIG. 12 in an inflated shape where about 2.5 ml of air have been placed into the balloon and cannula.

FIG. 14 is another side view of the access device 30 on the endoscope 100 where about 2.5 ml of air have been placed into the balloon 60c and catheter 70. At this air volume, the distal dome 64c maintained substantially the same shape, but the at least one base portion 66c domed slightly and pushed the distal dome 64 c and guide tip 62 in the distal direction. This increased the sum of longitudinal lengths A2 and B2 to about 11.7 mm without an appreciable change in D2. It is visually seen that the majority of the 0.7 mm balloon longitudinal length change occurred in the doming of the at least one base portion 66c which increased dimension B2. Pushing on the distal guide tip 62 so that it is embedded within the balloon created a slightly smaller dish shaped indent with the guide tip 62 standing proud in the indent. The increased volume of fill also increased the resistance to movement of the tip 62. The balloon 60c did not appear to move longitudinally from pushing on the guide tip 62 but expanded radially when filled with 2.5 ml of air.

Figure 15:
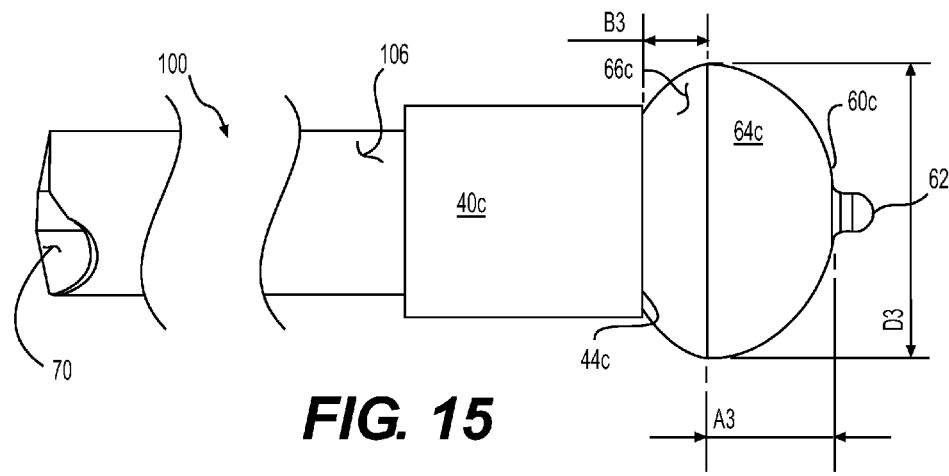
FIG. 15 shows the balloon of FIG. 12 in an inflated shape where about 3.5 ml of air have been placed into the balloon and cannula.

FIG. 15 is another side view of the access device 30 on the endoscope 100 where about 3.5 ml of air have been placed into the balloon 60c and catheter 70. Once again, the distal dome 64c maintained substantially the same shape and the at least one base portion 66c continued to move towards a dome shape. The longitudinal length (sum of A3 and B3) increased to about 12.2 mm with the majority of the 0.5 mm additional length increase coming from additional doming of the at least one base portion 66c. The dimension D3 increased slightly to 18.73 mm. When the guide tip 62 was pushed distally into the balloon 60c, the distal guide tip 62 had substantial resistance. Pushing on the distal guide tip 62 so that it is embedded within the balloon created a noticeably smaller dish shaped indent with the guide tip 62 standing proud in the indent. As the guide tip 62 was embedded into the balloon 60c, the balloon 60c also moved distally as some of the distal movement of the guide tip 62 was transferred to the balloon 60c. Visually, it appears that there is about the same amount of distal longitudinal movement of the balloon 60c as there is distal embedding of the guide tip 62. The distal movement of the balloon 60c is primarily in the at least one base portion 66c.

Figure 16:
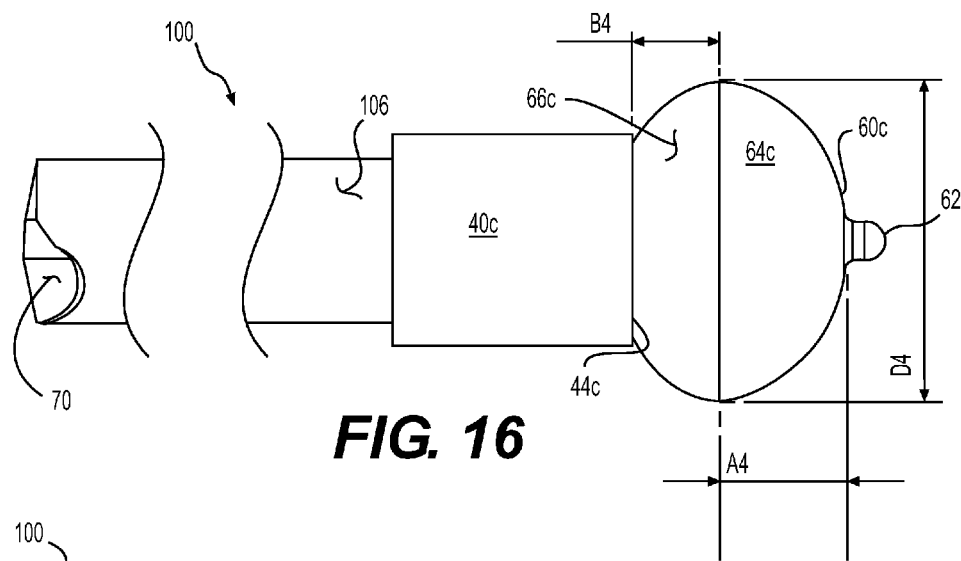
FIG. 16 shows the balloon of FIG. 12 in an inflated shape where about 5 ml of air have been placed into the balloon and cannula.

FIG. 16 is another side view of the access device 30 on the endoscope 100 where about 5 ml of air have been placed into the balloon 60c and catheter 70. The diameter D4 reduced back to the original 18 mm diameter and the longitudinal length (sum of A4 and B4) increased to about 14.75 mm. Once again, the majority of the additional length increase (2.55 mm) appears to be coming from additional doming of the at least one base portion 66c. There was some additional rounding of the distal dome 64c which may account for some of the reduction in overall diameter D4 and some of the length change. With respect to pushing distally on the guide tip 62 with 5 ml of air, the guide tip 62 has substantial resistance and the combination of balloon geometry (mushroom shape), fill volume (ml) balloon membrane 65c thickness and material durometer have combined to provide an unexpected shift in load transfer that seems to prevent the guide tip 62 from creating much of a dish indent in the balloon. With this fill volume, a substantial portion of the movement of the guide tip 62 towards the catheter 70 comes from a longitudinal compression of the balloon 60c to a different elliptical shape, and not from dishing the guide tip 62 into the balloon 60. This effect may be advantageous to tunneling through non-insufflated tissue lumens to maintain the distalmost positioning of the guide tip 62 during airless burrowing of the access device 30 and the endoscope 100. It is the distalmost position of the guide tip 62 which can enable the guide tip 62 to initiate separation of the collapsed luminal tissue. Once the initial separation occurs, the collapsed tissue separation may then be transferred to the outer surface of the balloon 60c as the access device 30 and endoscope 100 advances along the GI tract.

Figure 17:
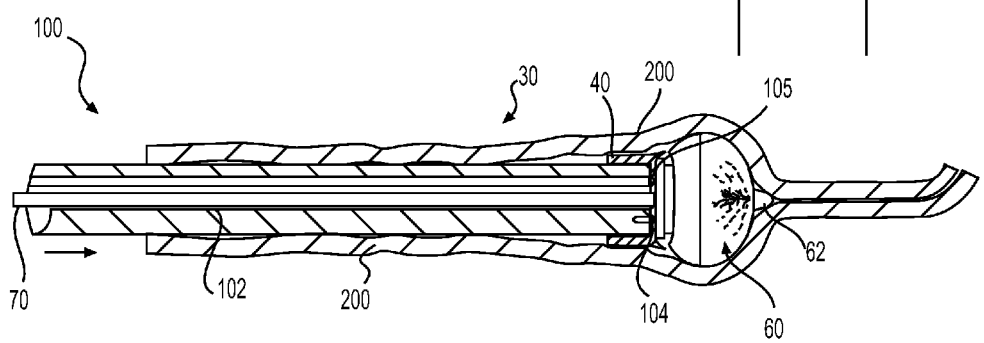
FIG. 17 is a side cross sectional view of the balloon access device installed upon an endoscope as the balloon access device spreads tissue to burrow through non-insufflated and collapsed luminal tissue.
Figure 18:
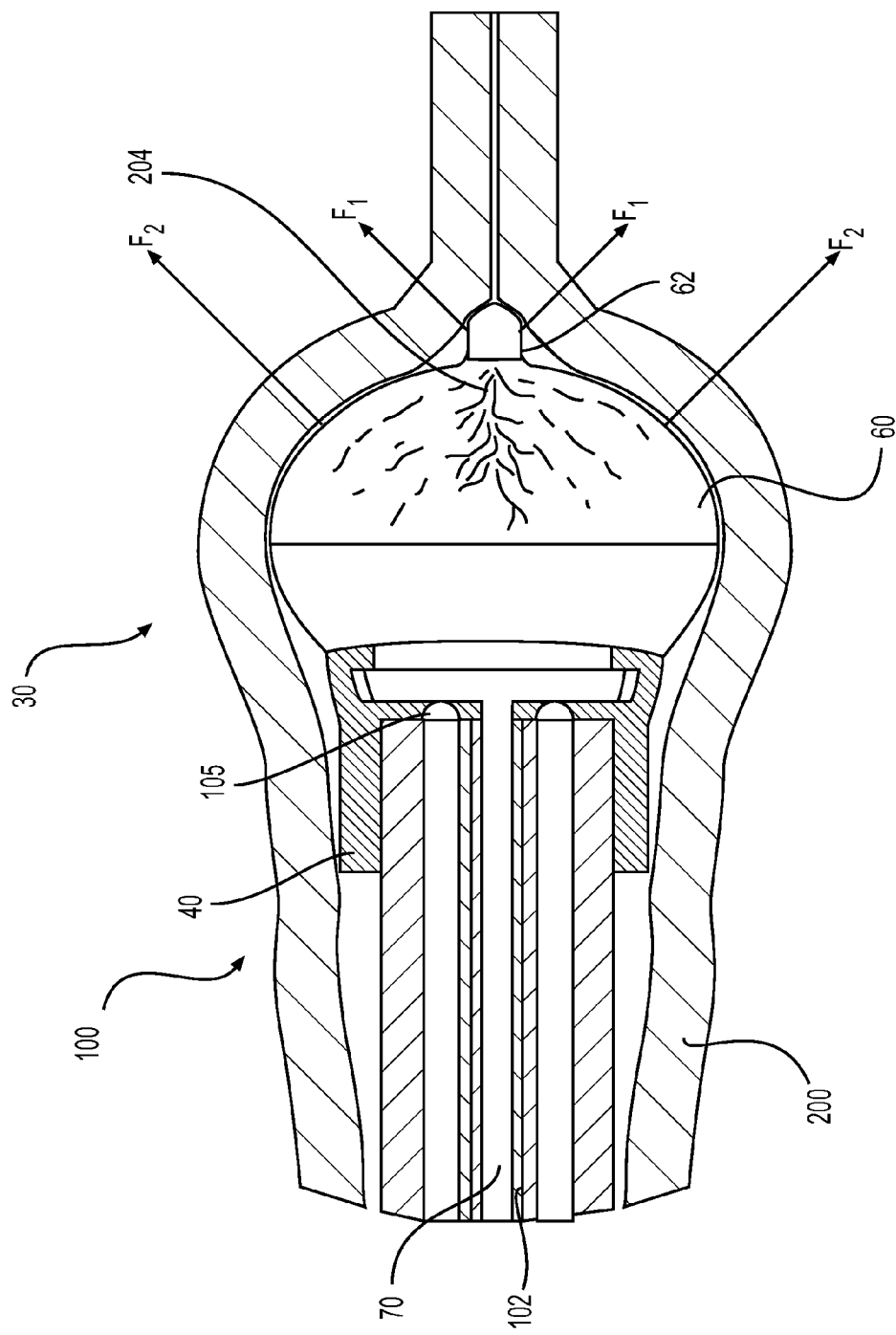
FIG. 18 is an enlarged side cross sectional view of the balloon access device of FIG. 17 showing spreading forces on the collapsed luminal tissue.

FIGS. 17 and 18 are side cross sectional views of the balloon access device 30 installed upon an endoscope 100 as it burrows through non-insufflated luminal tissue of the GI tract. FIG. 18 is an enlarged view of a portion of the cross sectional view of FIG. 17. As shown, the luminal tissue has collapsed, and the balloon access device 30 is providing both a visualization pocket and a tissue separator for the operator of the endoscope 100 so that the endoscope 100 can be easily advanced farther into the patient. An arrow is provided to indicate the direction of movement of the balloon access device 30 and endoscope 100. In this cross section, the collapsed luminal tissue 200 is partially spread by the balloon access device 30 and endoscope 100 as it burrows towards a bend in the tissue 200. The endoscope 100 is shown in cross section and has the operative channel 102 and front face 104 shown. Front face 104 of the scope 100 further comprises a lens 105 that views tissue through the transparent balloon 60. A viewing angle of the lens 105 is shown as dashed lines extending from the lens 105 (see FIG. 18). To prevent reduction of the viewing angle, the cap 40 may protrude above the front face 104 of the scope between about 0.5 mm to about 6 mm. Alternately, the cap 40 may protrude above the front face 104 of the scope between about 1 mm to about 3 mm. If desired, the vacuum in the endoscope 100 can be used to draw the balloon 100 against the front face 104 and the lens 105 of the endoscope 100. The hollow catheter 70 extends longitudinally along the operative channel 102 and is attached to the balloon 60 which is inflated (via the catheter 70) an amount that substantially restricts the embedding of the guide tip 62 into the balloon as described previously. The cap 40 is sealed against the endoscope and the balloon 60 is sealed within the cap 40 to seal the front face 104 of the endoscope 100 from fluids, mucous, and residual natural materials normally found within the luminal structure. As shown, ring 61 of the balloon is embedded in the groove 41 in the seal cap 40 to create a seal.

FIG. 18 is an enlarged side cross sectional view of FIG. 17. In this view, the spreading of the collapsed opening 204 of the tissue 200 can be seen through the transparent balloon 60. The lens 105 of the endoscope can be seen with dashed lines indicating a field of view through the balloon access device 30. Arrows show how a spreading force F1 is applied from the guide tip 62 onto the tissue 200. The guide force F1 is perpendicular or normal to the point of contact on the tissue. A second spreading force F2 is exerted on the tissue by the inflated balloon 60. Once again, the spreading force F2 is perpendicular or normal to the point of contact of the membrane 65 of the balloon 60 on the tissue.

Figure 19:
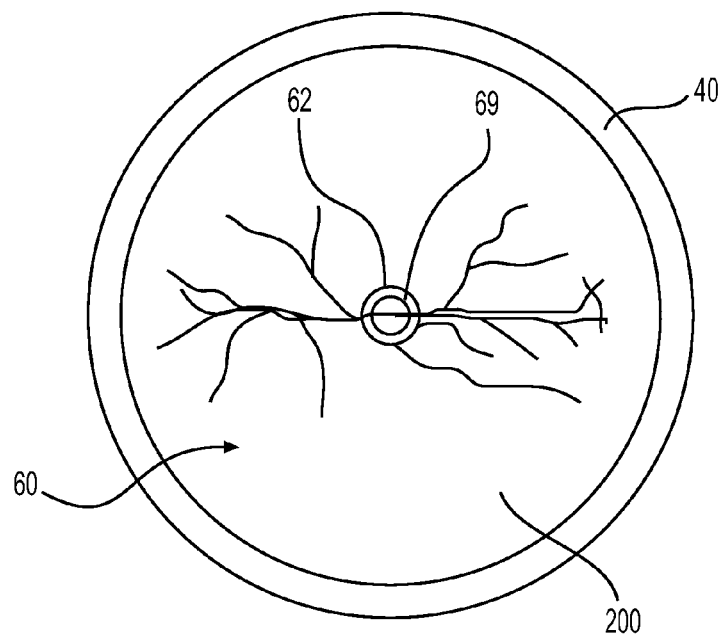
FIG. 19 is a view through the camera lens of the endoscope showing a guide tip of the balloon moved to a centered position in a collapsed tissue lumen opening to ensure passage of the balloon and endoscope down a center of the lumen.

FIG. 19 is a view through the lens 105 of the camera of the endoscope 100 looking at collapsed tissue through the transparent balloon 60 and guide tip 62. In this view, the surgeon has steered the guide tip 62 of the balloon 60 to a centered position of the collapsed tissue opening 204 of the tissue 200. Since the tissue guide 200 is transparent, tissue 200 can be seen therethrough. Once the guide tip 62 of the balloon 60 is centered, the surgeon is confident that the balloon access device 30 and endoscope 100 are aimed at the center of the collapsed lumen, and that the balloon access device 30 and endoscope 100 can now be pushed down a center of the lumen such as the large intestine. During testing of the device in actual tissue, several of the medical professional operators were surprised at the depth of penetration of the balloon access device 30 equipped endoscope 100 in such a short time.

Figure 20:
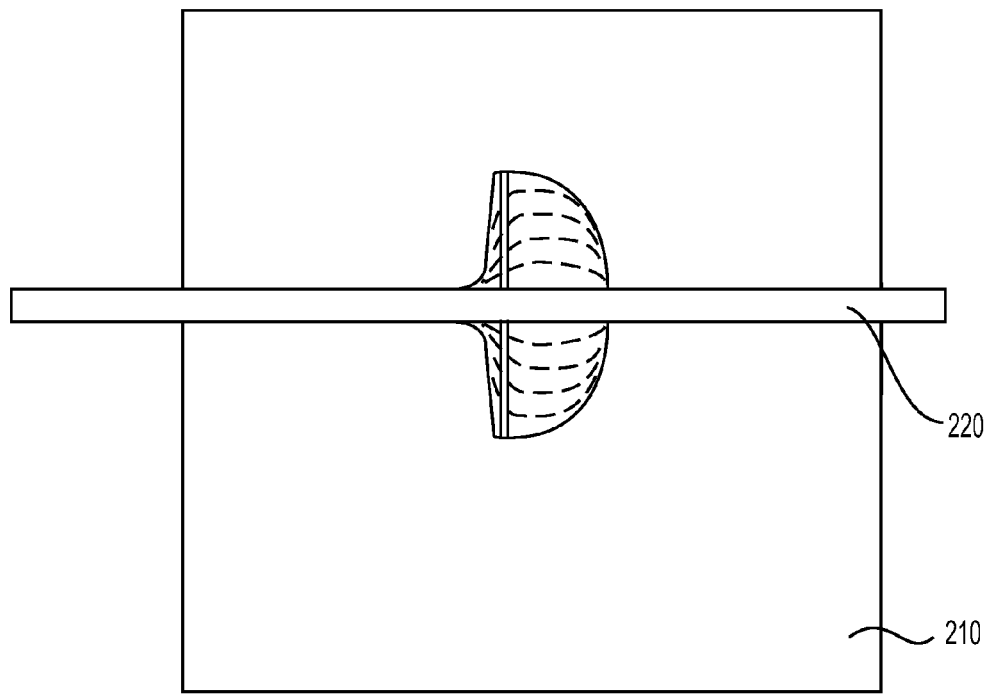
FIG. 20 is a cross sectional view of a blow molding dies that is configured to make the balloon of FIG. 12.

FIG. 20 is a cross sectional view of a blow molding dies that is configured to make the balloon of FIG. 12. As shown, the blow molding die 210 has a piece of expandable polyethylene tubing 220 placed along a longitudinal axis of the balloon shape of the die 210. Once the tubing 220 is heated, warm compressed air can be blown to expand the polyethylene tubing 220 against the cooler inner walls of the mold 210 which can be held slightly below the melting temperature of the polyethylene tubing 220. When the flow of warm expansion air is shut off, the tubing 220 has expanded against the walls of the mold 210 and sets in the net or normal "as manufactured" shape. Then the molded balloon 60 can be extracted by opening the die 210 to release the balloon 60. The dashed lines show the expansion stages of the polyethylene tubing 220 as it expands towards the mold walls 210. The natural tendency of the hot tubing 220 is to expand as a sphere until the expanding material contacts the walls of the die 210. As a consequence, different portions of the balloon membrane 65 (see FIG. 2) will be thinner than others and may taper between the thick and thin portions. For example, the portions of the tubing 220 that form the elongated projecting portion 68 and distal collar 67 will expand not at all or very slightly and will be thicker than the balloon membrane 65 at the points of largest expansion away from the longitudinal axis. The shape of the balloon can affect the location of the thick and thin membrane 65 portions and a stiffened disk may be found near the elongated projecting portion 68 and distal collars 67, which can affect the manner in which the balloon 60 expands (see FIGS. 13-16). This thickening could affect or restrict the displacement of the guide tip 62 from tissue contact by creating a more rigid "island" of membrane 65 around the distal tip 62 that may explain the deflection behavior described previously. In an alternate embodiment, the balloon 60 can be further stiffened in local areas by a dipping process to build up the balloon wall thickness. For example, the same material as the balloon membrane 65 can be used (such as polyurethane), or alternate dipping material may be used.

Figure 21:
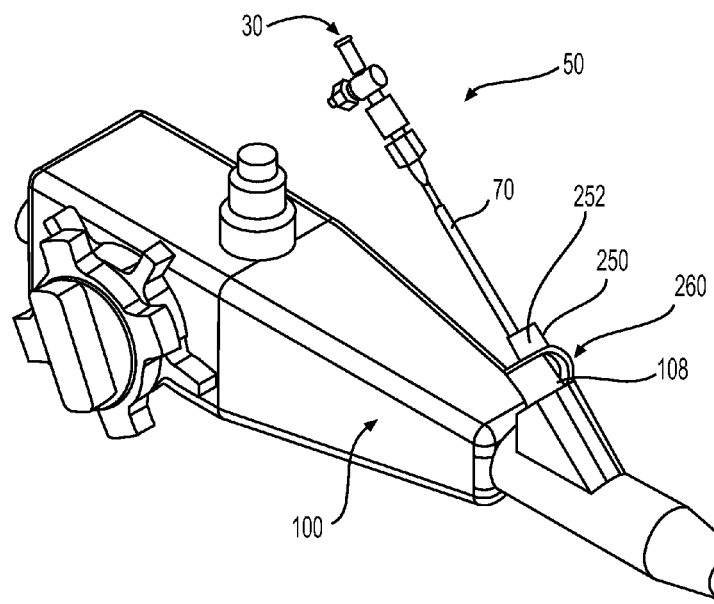
FIG. 21 is an isometric view of a clamp mechanism to clamp or lock the tensioned cannula relative to the endoscope to maintain a sealing contact between balloon and seal cap.

With some embodiments of the balloon such as that found in FIG. 12, a tension or pulling force may be applied to the catheter 70 to pull the balloon 60c into contact with the seal cap 40c to create a seal. It may be further desirable to include a lock or clamp mechanism 250 to hold the catheter 70 relative to the endoscope to ensure that the fluid tight seal is maintained in all tissue contacting situations. FIG. 21 illustrates an embodiment of a clamp mechanism 250 that can be used to clamp or lock the tensioned catheter 70 relative to the endoscope 100 to maintain a sealing contact between balloon 60c and seal cap 40c. Clamp mechanism 250 comprises a releasably lockable clamp mechanism that contacts and grips catheter 70 and is actuated and released via a pull member 252 to clamp the catheter 70. Alternate clamp mechanisms such as clamp mechanism 260 can surround the catheter 70 and retain it in place via frictional contact. One example of clamp member 260 would be a biopsy valve 108 or an adaption thereof wherein the biopsy valve 108 grips the endoscope 100 and the catheter 70 with an elastomeric material. And, in yet another embodiment of a clamp mechanism, the proximal balloon collar 63 may be configured to expand within the operative channel 102 of the endoscope 100 to lock the inflated balloon to the end of the endoscope. When the balloon is deflated, the proximal collar 63 unlocks from the operative channel 102.

Figure 22:
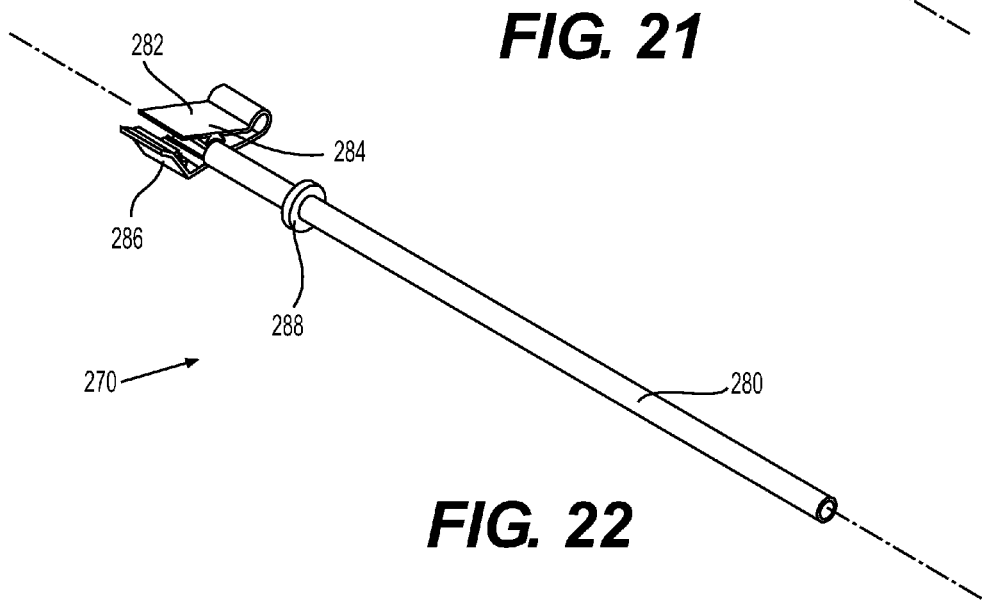
FIG. 22 is an alternate a clamp mechanism.

FIG. 22 shows an alternate embodiment of a clamping mechanism 270 that could be configured to replace the previously described hollow balloon insertion tube 80 with a clamping mechanism 270 that combines a hollow balloon insertion tube 280 with a user actuated clamp 282. The clamping mechanism 270 has a longitudinal hollow that would slide freely over the catheter 70 and the collapsed balloon 60c could reside within (not shown). The hollow balloon insertion tube 280 can be configured to fit within the operative channel 102 of the endoscope and the biopsy valve 108 (if provided). The hollow balloon insertion tube 280 may be sized to be inserted into the operative channel 102 to a position past a "Y" branch of the channel 102. The collapsed balloon 60c can then be introduced into the operative channel 102 of the endoscope 100 without direct contact with the "Y". Once the balloon 60c was extended from the scope and inflated, the clamping mechanism 270 could be pushed inward to bring a stop collar 288 into contact with the proximal opening of the operative channel, or the biopsy valve 108 (if present). Pulling on the handle 50 or the catheter 70 while pushing on the clamping mechanism 270 can ensure a seal between the balloon 60c and the seal cap 40c (not shown). Locking the user actuated clamp 282 ensures the seal is locked and maintained between balloon 60c and the seal cap 40c. As shown in FIG. 22 but not limited thereto, the user actuated clamp 282 can comprise a deflectable cantilever beam 284 that can, when deflected, simultaneously clamp on the catheter 70 and lock with a clamp arm 286. The clamp arm 286 can also be a cantilever, and can be deflected to release the deflectable cantilever beam 284 to unlock the user actuated clamp 282, and to release the catheter 70. Stop collar 288 can be used to contact and push against the endoscope or the biopsy valve 108 to maintain tension on the catheter 70.

Figure 23:
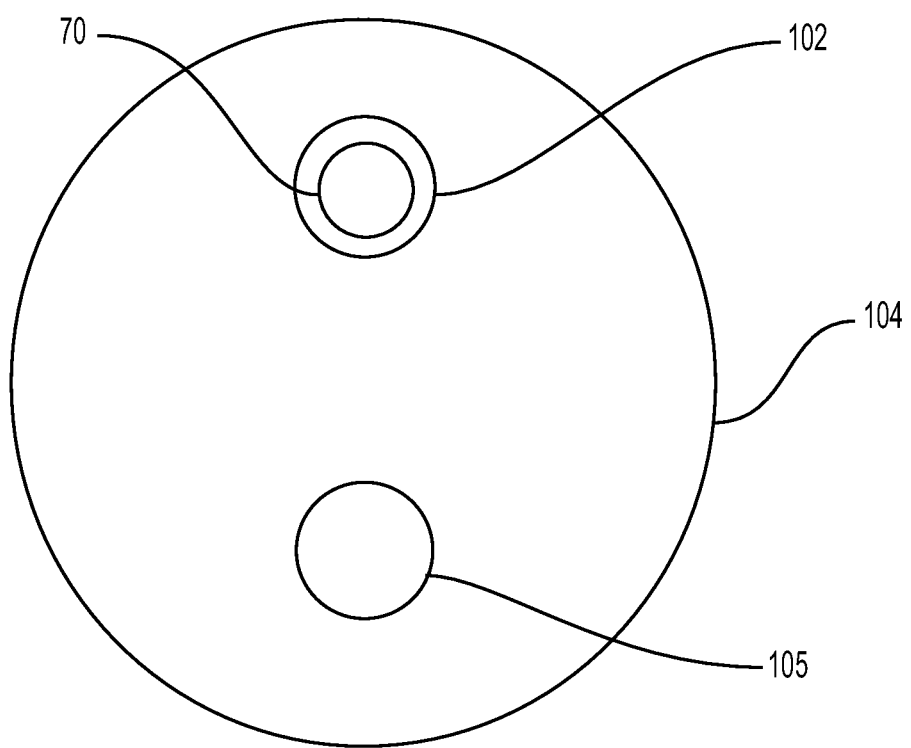
FIG. 23 is a front view of a distal end of an endoscope.

Turning now to FIG. 23, a front view of the front face 104 of the endoscope is shown. The operative channel 102 of the endoscope is non-concentrically disposed in the endoscope, and accordingly the catheter 70 and balloon are non-concentrically disposed relative to a central axis of the endoscope. As described previously, when the cap 40 and balloon 60 are installed on the endoscope, pulling on the catheter seals the balloon 60 against the cap 40 and the non-concentrically disposed balloon 60 is free to pivot somewhat about the attachment point to the catheter 70 to center itself in the seal cap 40.

During operation, as the balloon 60 pushes tangentially against the intestinal wall, the force attempts to unseat the balloon from the cap. The flaring portions of the cap, shown in FIG. 9 for example, seat the balloon to prevent the seal between the balloon and the cap from being broken or otherwise compromised. Additionally or alternatively, the cap, for example the cap shown in FIGS. 9-12, may include one or more longitudinal cuts in a portion of the cap protruding past the distal end 106 of the endoscope to prevent the balloon from being unseated from the cap when the balloon pushes against the intestinal wall. Alternatively, the portion of the cap protruding past the distal end 106 of the endoscope may have portions of varying heights to seal with the balloon.

FIGS. 24-30 depict balloon and endoscope embodiments that are configured for use with or without cap 40. These balloon embodiments may optionally have the same or similar dimensions as balloon 60c of FIGS. 13-16. As demonstrated in the cross sections of FIGS. 24A-C, the balloons 60d, 60e, and 60f may be positioned such that the elongated projecting portion 68 of proximal collar 63 inflates to contact the operative channel 102 of the endoscope. After at least partial inflation, the user may pull back on the catheter 70 to bring the base portion 66 of proximal collar 63 into contact with the lens 105 (over the visualization channel 107). The transparent nature of the balloon allows for the visualization of the intestinal surfaces through both the proximal and distal ends of the balloon 60d, 60e, or 60f. Inflation of the proximal projecting portion 68 against the wall of the operative channel 102 stabilizes the balloon to prevent it from sliding off the lens 105. This improves the clarity of the image that is transmitted to the user though visualization channel 107 by preventing fluids from reaching the lens 105. An illumination channel 109 and light 111 may also be included on these or other embodiments to assist in visualization of the intestinal wall. The illumination channel and light may be covered by the base portion 66 of the balloon in its partially or fully inflated state, such that the light is directed through the base portion and the distal dome 64 to illuminate the intestinal wall. In FIGS. 24A-C, the operative channel 102 is positioned around the longitudinal center of the endoscope 100. However, other embodiments may include an operative channel that is off-center as shown in FIG. 23.

Figure 24A:
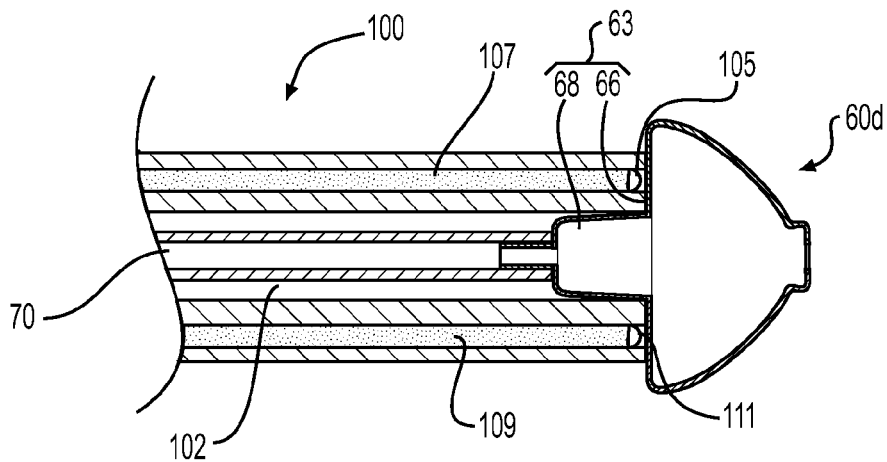
FIG. 24A is a side section of an endoscope with an inflated balloon.
Figure 24B:
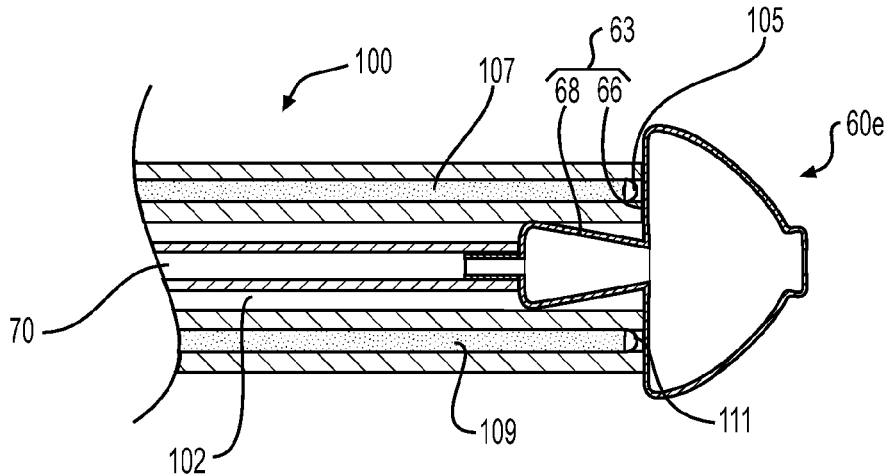
FIG. 24B is a side section of an endoscope with another embodiment of an inflated balloon.
Figure 24C:
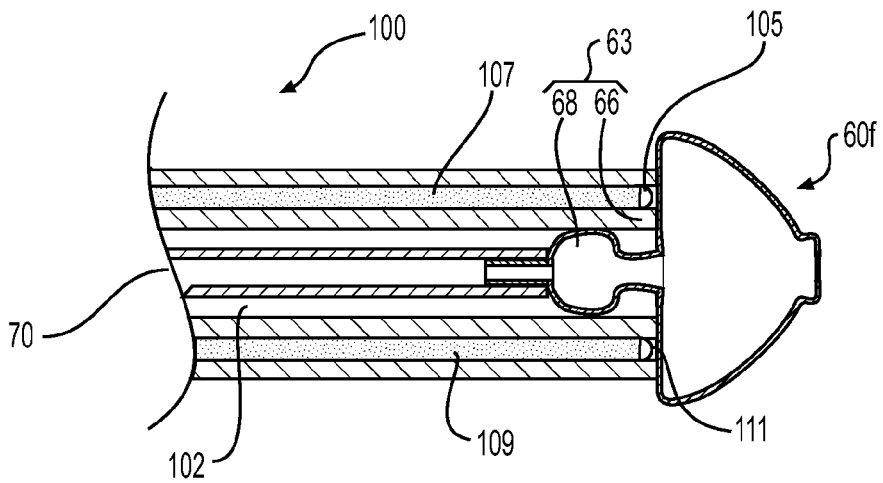
FIG. 24C is a side section of an endoscope with another embodiment of an inflated balloon.

As seen in FIGS. 24A-C, the proximal collar 63 may take different shapes. For example, balloon 60d of FIG. 24A may have a collar with a shaped portion that is pyramidal or tapered. Balloon 60e of FIG. 24B may also have a collar with a shaped portion that is pyramidal or tapered in the opposite direction as the taper of balloon 60d. Balloon 60f of FIG. 24C may have a collar with a shaped portion that is bulbous. In some embodiments, the shaped portion is part of the proximal elongated projecting portion 68 of the proximal collar 63. For example, FIG. 24A shows a proximal collar 63 with a proximal projecting portion 68 that projects into the operative channel 102 of the endoscope. In this embodiment, the shaped portion is tapered and located on the proximal projecting portion 68. The wider end of the taper is positioned adjacent the base portion 66 of the proximal collar 63.

Figure 25:
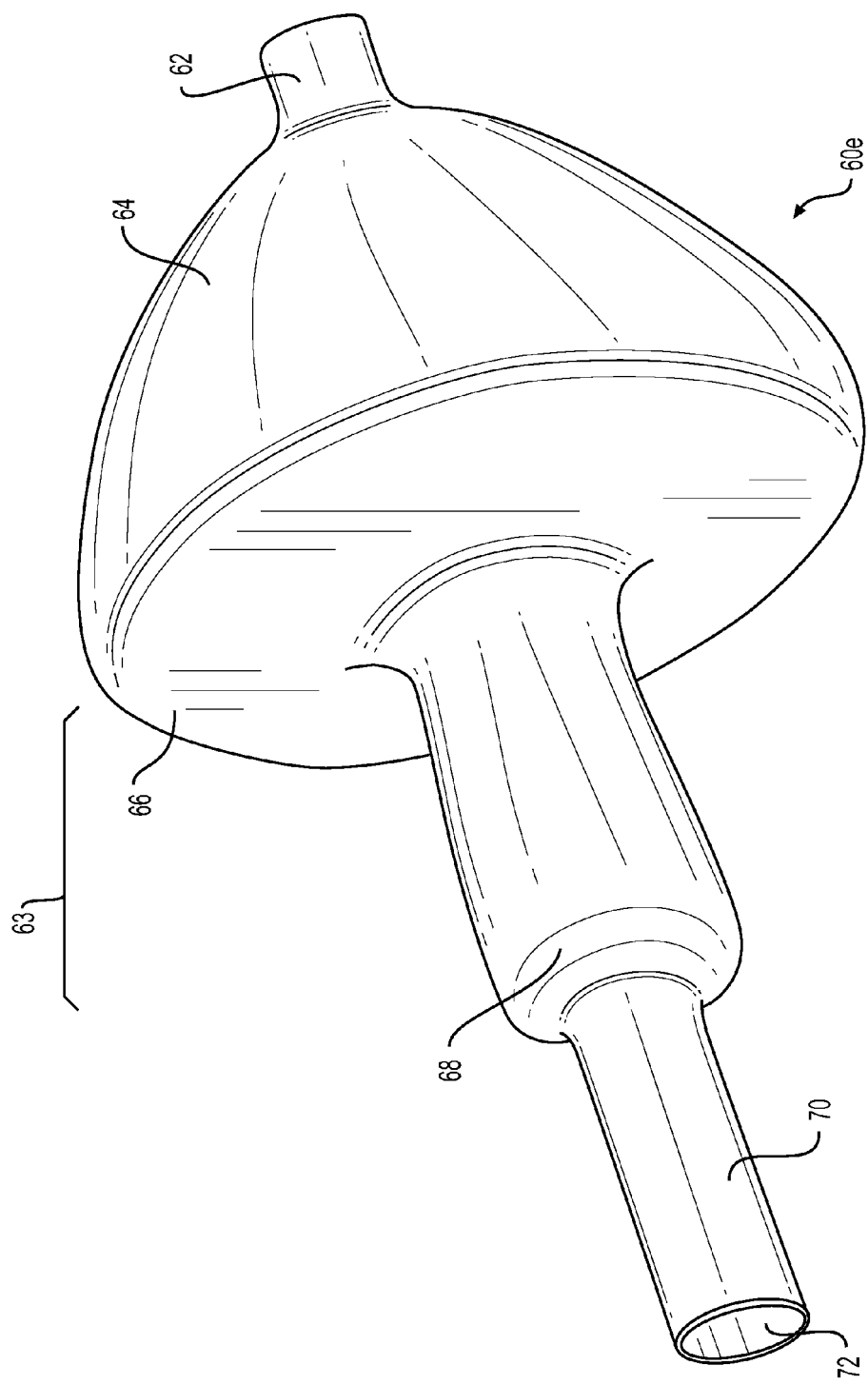
FIG. 25 is a perspective view of a balloon.
Figure 26A:
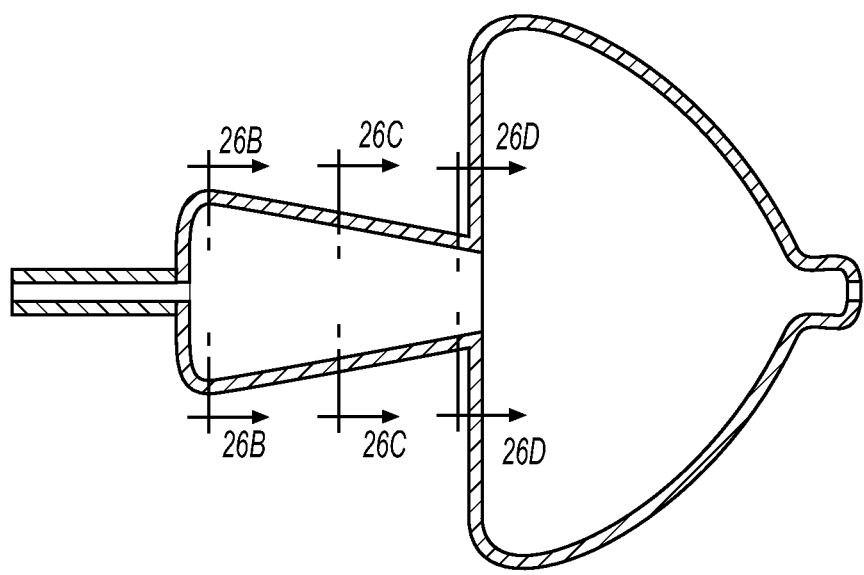
FIG. 26A is a side section of a balloon.

Alternatively, the narrower end of the taper may be positioned adjacent the base portion 66 as shown in FIG. 24B. In other embodiments, such as the one shown in FIG. 24C, the shaped portion may be bulbous. The bulbous shaped portion may be spaced from the base portion 66, as shown, or it may be positioned adjacent the base portion. FIG. 25 is a perspective view of a balloon with a tapered proximal projecting portion, similar to the embodiment of FIG. 24B. FIG. 26A is a side view of a balloon similar to FIG. 24 B. In 26A, section lines are drawn along the proximal projecting portion 68. These section lines indicate the transverse cross-sectional views shown in FIGS. 26B-D.

Figure 27:
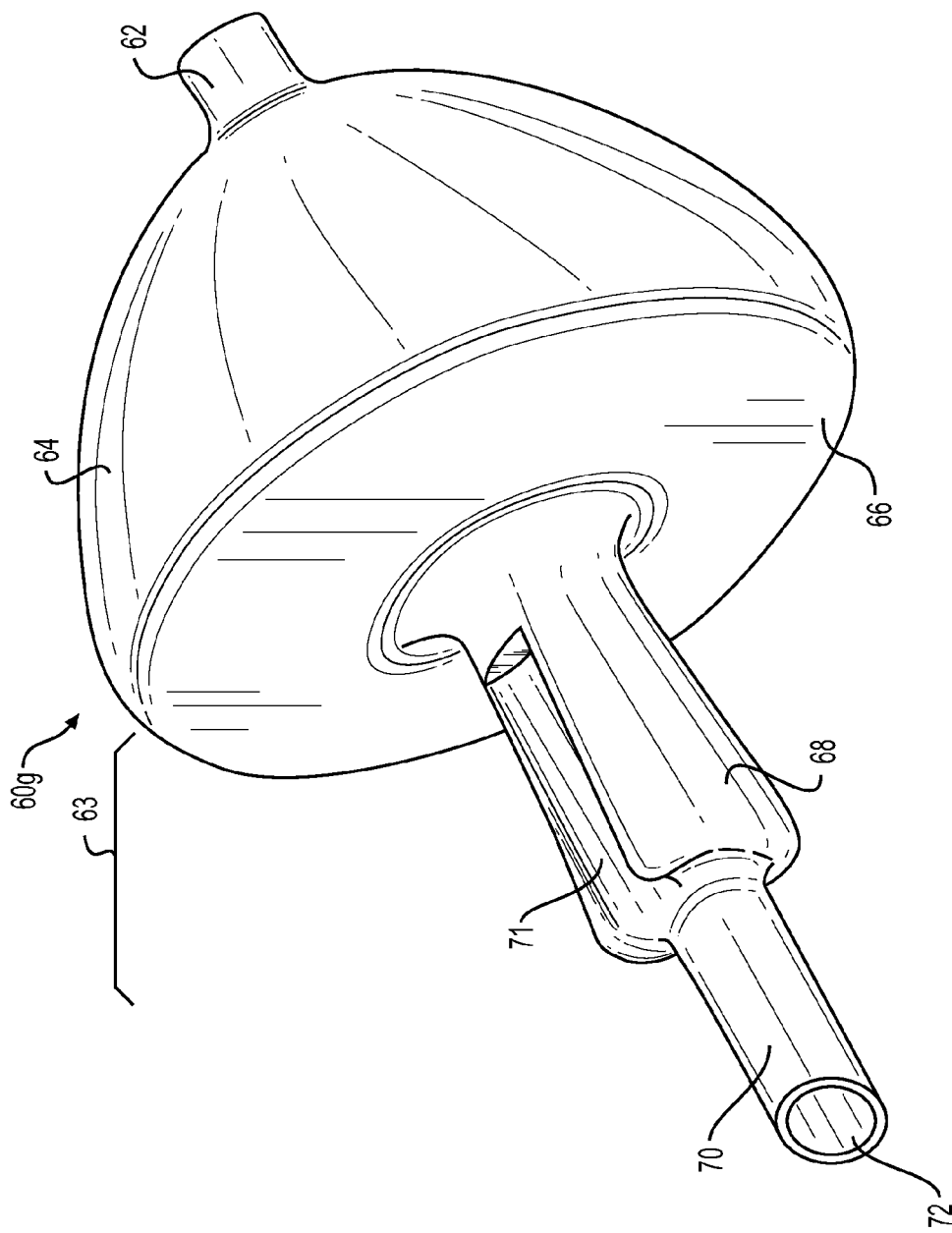
FIG. 27 is a perspective view of a balloon including longitudinal grooves.

FIG. 27 shows an embodiment of a balloon 60g configured for use with or without the cap 40. This embodiment includes a tapering shaped portion, similar to the embodiment of FIG. 25, as well as a longitudinal groove 71 on the proximal collar 63. The embodiment shown has one groove, but embodiments may have multiple grooves. For example, some embodiments may have 2, 3, 4, 5, 6, 7, 8, 9, or 10 grooves. The grooves 71 may extend only along the proximal projecting portion 68, or may start on the proximal projecting portion and continue along the base portion 66. The grooves may take various shapes when viewed in transverse cross-section. For example, the grooves 71 may be any polygonal shape, or the shape of a segment or sector of a circle or ellipse. For example, the grooves may be hemispherical or trapezoidal in shape. Alternatively, the grooves when viewed in transverse cross-section may have multiple portions, and each portion may take the shape of a polygon or a segment or sector of a circle or ellipse. In some embodiments, grooves 71 allow the user to eject fluid around the projecting portion 68 of the proximal collar 63 for assistance in cleaning the lens 105 while projecting portion 68 is inflated and abutting the walls of the operative channel 102. Alternatively, the grooves 71 may be used to activate a suction between the operative channel 102 of the endoscope and the intestinal environment.

FIG. 28 shows an embodiment of a balloon 60h configured for use with or without the cap 40. This embodiment includes a tapering shaped portion, similar to the embodiment of FIG. 25, and also includes longitudinal grooves 71 and trusses 73. The balloon may have multiple trusses, for example 2, 3, 4, 5, 6, 7, 8, 9, 10, 11, 12, 13, 14, 15, 16, 17, 18, 19, 20 or more trusses. The trusses 73 may be of any shape. For example, the trusses 73 may be cylindrical, ellipsoidal, or polygonal in shape. The trusses may extend from at least one proximal point to at least one distal point on the proximal collar 63. For example, trusses 73 may extend along only the proximal projecting portion 68, only along the base portion 66, or along both portions 66 and 68 of collar 63. The trusses may act as architectural reinforcements to stabilize the balloon, keeping it in contact with the distal face of the endoscope 104 and the lens 105.

The inclusion of grooves 71 or trusses 73 may give part of the proximal collar 63 a sun beams-shaped pattern when viewed in transverse cross-section (perpendicular to the longitudinal axis of the balloon). The rays of the sun beams shape are areas that thicken the wall of the balloon, such as the trusses 73 of the embodiment in FIG. 28. The sun beams-shaped pattern includes indentations between the rays. In some embodiments, these indentations may be grooves 71, or spaces between trusses 73. The indentations may be configured to engage at least one protrusion on an underlying surface, such as the distal face 104 or operative channel 102 of the endoscope 100. In some embodiments, the protrusion is the lens 105. The user may position the balloon to optimize visualization after inflation, for example by rotating the balloon such that an indentation mates with the lens 105. This allows the lens to image through a thinner area of the balloon wall, improving visualization of the intestinal structures.

While the present medical apparatus has been illustrated by description of several embodiments, additional advantages and modifications may readily appear to those skilled in the art. For example, in some embodiments, the seal cap 40 can be configured to grip the balloon 60 and the endoscope 100, thereby securing the balloon 60 to the endoscope 100.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A balloon access device for use with an endoscope, the endoscope comprising an operative channel with a distal opening and a visualization channel, the balloon access device comprising:
   a) a balloon comprising a proximal end and a distal end having a dome portion, wherein the balloon is inflatable or deflatable;
   b) wherein the proximal end of the balloon comprises an inflatable or deflatable collar, the collar comprising a proximal elongated projecting portion and a base portion located distal to the projecting portion, and wherein the projecting portion is configured to project proximally within the operative channel;
      i) wherein the proximal elongated projecting portion has a central long axis and a taper; and
      ii) wherein a narrower end of the taper is positioned adjacent the base portion of the collar; and c) wherein the base portion of the collar is configured for positioning over the visualization channel when the projecting portion projects within the operative channel such that imaging using the endoscope visualization channel includes a transmission of light through the base portion and the distal end of the balloon.

2. The balloon access device of claim 1, wherein the balloon is transparent and devoid of internal structure.

3. The balloon access device of claim 1, wherein the proximal end of the balloon comprises an opening that is in fluid communication with an interior space of the balloon.

4. The balloon access device of claim 1, wherein the operative channel of the endoscope is spaced from a longitudinal central axis of the endoscope.

5. The balloon access device of claim 1, wherein an outer surface of the collar comprises at least one groove.

6. The balloon access device of claim 5, wherein the groove is located on the projecting portion, the base portion, or both.

7. The balloon access device of claim 5, wherein the grooves extend from a proximal point on the collar to a distal point on the collar.

8. The balloon access device of claim 5, wherein the grooves comprise at least one transverse cross section along their length, a shape of the transverse cross section comprising at least one of a polygon, a sector of a circle or ellipse, and/or a segment of a circle or ellipse.

9. The balloon access device of claim 8, wherein the transverse cross section comprises multiple portions, and each portion may have the shape of a polygon, a sector of a circle or ellipse, or a segment of a circle or ellipse.

10. The balloon access device of claim 1, wherein the collar further comprises trusses.

11. The balloon access device of claim 10, wherein the trusses comprise at least one transverse cross section along their length, a shape of the transverse cross section comprising at least one of cylindrical, ellipsoidal and/or polygonal.

12. The balloon access device of claim 10, wherein the trusses extend from at least one proximal point on the collar to at least one distal point on the collar.

13. The balloon access device of claim 10, wherein the trusses extend along the proximal elongated projecting portion of the collar.

14. The balloon access device of claim 13, wherein the trusses continue distally to extend along the base portion of the collar.

15. The balloon access device of claim 1, wherein at least one part of the proximal collar comprises a sun beams-shaped pattern in transverse cross section, the sun beams-shaped pattern comprising multiple rays extending from a central point, and multiple indentations between the rays.

16. The balloon access device of claim 15, wherein at least one indentation of the sun beams pattern is configured to mate with at least one protrusion on an underlying surface.

17. The balloon access device of claim 16, wherein the protrusion is located on at least one of the distal face of the endoscope and/or an interior lumen of the endoscope.

18. The balloon access device of claim 17, wherein the protrusion is a lens in optical communication with the visualization channel of the endoscope.

19. The balloon access device of claim 1, further comprising a catheter configured to move proximally and distally within the operative channel of the endoscope.

20. The balloon access device of claim 19, wherein the collar of the balloon extends over a distal end of the catheter such that the balloon is in fluid communication with an internal lumen of the catheter.

21. A method of visualizing a internal surface of an intestinal cavity of a patient, the method comprising
a) providing the balloon access device of claim 20,
b) positioning a portion of the balloon access device within the intestinal cavity of the patient,
c) moving the catheter within the operative channel of the endoscope such that at least one portion of the balloon is extending beyond a distal end of the endoscope,
d) inflating the balloon,
e) positioning the balloon to promote contact between the base portion of the collar and a lens positioned on a distal face of the endoscope, the lens being in optical communication with the visualization channel of the endoscope, and
f) maneuvering the balloon to visualize the internal surface of the intestinal cavity.

22. The method of claim 21, further comprising assembling the balloon access device outside of a patient to promote optimal visualization through the base portion of the balloon during operation of the device.

23. The method of claim 21, further comprising activating an optical communication system comprising the lens and the visualization channel of the endoscope.

24. The method of claim 21, further comprising delivering fluid to the intestinal cavity through the operative channel of the endoscope.

25. The method of claim 21, further comprising creating a suction between the intestinal cavity and the operative channel of the endoscope.

26. The method of claim 21, wherein moving the catheter within the operative channel of the endoscope comprises pushing or pulling the catheter.

27. The method of claim 21, wherein positioning the balloon to promote contact comprises pulling the catheter proximally to cause the base portion of the balloon to abut the lens of the endoscope.

28. The method of claim 21, wherein at least one part of the collar of the balloon comprises a sun beams-shaped pattern in transverse cross section, the sun beams shaped pattern comprising multiple rays extending from a central point and multiple indentations between the rays, and wherein maneuvering the balloon to visualize comprises rotating the balloon until at least one indentation mates with at least one protrusion on the endoscope.

29. The method of claim 28, wherein the protrusion is the lens on the distal face of the endoscope.

* * * * *